(12) United States Patent
Condie et al.

(10) Patent No.: US 10,182,742 B2
(45) Date of Patent: *Jan. 22, 2019

(54) TISSUE CONTACT SENSING WITH A MULTI ELECTRODE ABLATION CATHETER

(71) Applicant: Medtronic Ablation Frontiers LLC, Minneapolis, MN (US)

(72) Inventors: Catherine R. Condie, Shoreview, MN (US); Steven J. Fraasch, Maple Grove, MN (US); Marshall L. Sherman, Cardiff By The Sea, CA (US); Trenton Jay Rehberger, Minneapolis, MN (US); Corinne Weyrauch, Brooklyn Park, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 828 days.

This patent is subject to a terminal disclaimer.

(21) Appl. No.: 14/677,731

(22) Filed: Apr. 2, 2015

(65) Prior Publication Data

US 2016/0287136 A1 Oct. 6, 2016

(51) Int. Cl.
*A61B 5/06* (2006.01)
*A61B 8/14* (2006.01)
(Continued)

(52) U.S. Cl.
CPC ............ *A61B 5/068* (2013.01); *A61B 5/0538* (2013.01); *A61B 5/6852* (2013.01);
(Continued)

(58) Field of Classification Search
CPC ..... A61B 5/068; A61B 5/0538; A61B 5/6852; A61B 5/6869; A61B 5/6886;
(Continued)

(56) References Cited

U.S. PATENT DOCUMENTS

| 5,341,807 A | 8/1994 | Nardella |
| 5,447,529 A | 9/1995 | Marchlinski et al. |

(Continued)

FOREIGN PATENT DOCUMENTS

| CA | 2607577 A1 | 11/2006 |
| CA | 2813627 A1 | 5/2012 |

(Continued)

OTHER PUBLICATIONS

International Search Report and Written Opinion dated Oct. 25, 2016, for corresponding International Application No. PCT/US2016/023736; International Filing Date: Mar. 23, 2016 consisting of 13-pages.

(Continued)

*Primary Examiner* — Thomas Hong
*Assistant Examiner* — Colin T Sakamoto
(74) *Attorney, Agent, or Firm* — Christopher & Weisberg, P.A.

(57) ABSTRACT

A method and system for assessing electrode-tissue contact before the delivery of ablation energy. The system may include a control unit programmed to determine a difference between a maximum impedance magnitude at a low frequency for a given electrode and an absolute minimum impedance magnitude at the low frequency across all electrodes, determine a difference between a maximum impedance magnitude at a high frequency for a given electrode and an absolute minimum impedance magnitude at the high frequency across all electrodes, and determine a difference between a maximum impedance phase at the high frequency for a given electrode and an absolute minimum impedance phase at the high frequency across all electrodes. Differences may be correlated to one another using a linear model, the results determining electrode-tissue contact status. The (Continued)

results may be displayed in a graphical format for easy communication to the user.

21 Claims, 21 Drawing Sheets

(51) Int. Cl.
- *A61B 5/00* (2006.01)
- *A61B 18/12* (2006.01)
- *A61B 5/053* (2006.01)
- *A61B 18/14* (2006.01)
- *A61B 18/00* (2006.01)

(52) U.S. Cl.
CPC .......... *A61B 5/6869* (2013.01); *A61B 5/6886* (2013.01); *A61B 5/7225* (2013.01); *A61B 5/7246* (2013.01); *A61B 18/1206* (2013.01); *A61B 5/7275* (2013.01); *A61B 5/743* (2013.01); *A61B 18/1492* (2013.01); *A61B 2018/0016* (2013.01); *A61B 2018/00267* (2013.01); *A61B 2018/00351* (2013.01); *A61B 2018/00577* (2013.01); *A61B 2018/00654* (2013.01); *A61B 2018/00672* (2013.01); *A61B 2018/00678* (2013.01); *A61B 2018/00702* (2013.01); *A61B 2018/00839* (2013.01); *A61B 2018/00875* (2013.01); *A61B 2018/00904* (2013.01); *A61B 2018/00982* (2013.01); *A61B 2018/1467* (2013.01); *A61B 2562/0209* (2013.01); *A61B 2562/04* (2013.01)

(58) Field of Classification Search
CPC . A61B 5/7225; A61B 5/7246; A61B 18/1206; A61B 18/1492; A61B 2090/065; A61B 2018/00577; A61B 2018/00642; A61B 2018/00869; A61B 2018/00875; A61B 2018/0016; A61B 2018/00351; A61B 2018/00654; A61B 2018/00672; A61B 2018/00702; A61B 2018/00904; A61B 2018/00982; A61B 2018/00267; A61B 2018/00839; A61B 2018/1467; A61B 2562/0209; A61B 2562/04; A61B 5/743; A61B 5/7275

See application file for complete search history.

(56) References Cited

U.S. PATENT DOCUMENTS

| | | | |
|---|---|---|---|
| 5,588,432 A | 12/1996 | Crowley | |
| 5,836,990 A | 11/1998 | Li | |
| 6,123,702 A | 9/2000 | Swanson et al. | |
| 6,186,147 B1 | 2/2001 | Cobb | |
| 6,217,574 B1 | 4/2001 | Webster | |
| 6,391,024 B1 | 5/2002 | Sun et al. | |
| 6,423,057 B1 | 7/2002 | He et al. | |
| 7,842,031 B2 | 11/2010 | Abboud et al. | |
| 7,914,525 B2 | 3/2011 | Abboud et al. | |
| 8,267,926 B2 | 9/2012 | Paul et al. | |
| 8,290,578 B2 | 10/2012 | Schneider | |
| 8,317,783 B2 | 11/2012 | Cao et al. | |
| 8,369,922 B2 | 2/2013 | Paul et al. | |
| 8,403,925 B2 | 3/2013 | Miller et al. | |
| 8,406,866 B2 | 3/2013 | Deno et al. | |
| 8,449,535 B2 | 5/2013 | Deno et al. | |
| 8,603,084 B2 | 12/2013 | Fish et al. | |
| 8,696,656 B2 | 4/2014 | Abboud et al. | |
| 8,728,077 B2 | 5/2014 | Paul et al. | |
| 8,755,860 B2 | 6/2014 | Paul et al. | |
| 2002/0068931 A1 | 6/2002 | Wong et al. | |
| 2005/0004644 A1* | 1/2005 | Kelsch | A61B 17/8888 607/131 |
| 2007/0270795 A1 | 11/2007 | Francischelli et al. | |
| 2008/0275465 A1 | 11/2008 | Paul et al. | |
| 2008/0281319 A1 | 11/2008 | Paul et al. | |
| 2008/0288038 A1 | 11/2008 | Paul et al. | |
| 2008/0300589 A1 | 12/2008 | Paul et al. | |
| 2009/0030477 A1 | 1/2009 | Jarrard | |
| 2009/0163904 A1 | 6/2009 | Miller et al. | |
| 2009/0171235 A1 | 7/2009 | Schneider et al. | |
| 2009/0177111 A1 | 7/2009 | Miller et al. | |
| 2009/0182318 A1 | 7/2009 | Abboud et al. | |
| 2009/0275827 A1 | 11/2009 | Aiken et al. | |
| 2009/0306643 A1 | 12/2009 | Pappone et al. | |
| 2010/0069921 A1* | 3/2010 | Miller | A61B 18/1233 606/130 |
| 2010/0168735 A1 | 7/2010 | Deno et al. | |
| 2010/0179538 A1 | 7/2010 | Podhajsky | |
| 2010/0228247 A1 | 9/2010 | Paul et al. | |
| 2010/0241117 A1 | 9/2010 | Paul et al. | |
| 2010/0286690 A1 | 11/2010 | Paul et al. | |
| 2010/0298823 A1 | 11/2010 | Cao et al. | |
| 2011/0106075 A1* | 5/2011 | Jimenez | A61B 18/1206 606/41 |
| 2011/0118727 A1 | 5/2011 | Fish et al. | |
| 2011/0144524 A1 | 6/2011 | Fish et al. | |
| 2011/0144657 A1 | 6/2011 | Fish et al. | |
| 2011/0264000 A1 | 10/2011 | Paul et al. | |
| 2012/0029504 A1 | 2/2012 | Afonso et al. | |
| 2012/0123400 A1 | 5/2012 | Francischelli et al. | |
| 2012/0197243 A1* | 8/2012 | Sherman | A61B 18/02 606/21 |
| 2012/0323237 A1 | 12/2012 | Paul et al. | |
| 2013/0023784 A1 | 1/2013 | Schneider | |
| 2013/0138099 A1 | 5/2013 | Paul et al. | |
| 2013/0226169 A1 | 8/2013 | Miller et al. | |
| 2013/0296840 A1* | 11/2013 | Condie | A61B 90/06 606/33 |
| 2014/0051959 A1* | 2/2014 | Gliner | A61B 5/6869 600/374 |
| 2014/0107430 A1 | 4/2014 | Deno et al. | |
| 2014/0180278 A1 | 6/2014 | Abboud et al. | |
| 2014/0194867 A1 | 7/2014 | Fish et al. | |
| 2014/0276712 A1 | 9/2014 | Mallin et al. | |

FOREIGN PATENT DOCUMENTS

| | | |
|---|---|---|
| CA | 2814985 A1 | 5/2012 |
| CN | 103379873 A | 10/2013 |
| EP | 1586281 B1 | 4/2009 |
| WO | 2011143199 A1 | 11/2011 |
| WO | 2012106100 A2 | 8/2012 |
| WO | 2013162884 A1 | 10/2013 |
| WO | 2014149925 A1 | 9/2014 |

OTHER PUBLICATIONS

D. H. Sheingold, "Impedance & Admittance Transformations Using Operational Amplifiers," Lightning Empiricist, vol. 12, No. 1, 1964, pp. 1-8. http://www.philbrickarchive.org/1964-1_v12_no1_the_lightning_empiricist.htm.

* cited by examiner

FIG. 6

| | Test Outcome (Algorithm Result) | Manually Assigned Outcome | |
|---|---|---|---|
| | | Good Contact | No Contact |
| | Good Contact | True Positive | False Positive |
| | No Contact | False Negative | True Negative |

FIG. 7

| | Impact on Algorithm Performance | Positive Impact | No Significant Impact | Negative Impact | N/A |
|---|---|---|---|---|---|
| Predictor Variables | Pre-ablation Predictors | X | | | |
| | Post-ablation Predictors | | | X | |
| | Pre- and Post-ablation Predictors | | | X | |
| Data Normalization | Normalization by Minimum Value | X | | | |
| | Normalization by Maximum Value | | | X | |
| | Rounding | | | | X |
| | Data Adjudication | | X | | |
| Development Group Data Set Composition | SVC and Non-SVC Ablations | | X | | |
| | SVC Ablations, Non-SVC Ablations Using Blood Measurements Only | X | | | |
| Test Group Data Set Composition | SVC and Non-SVC Ablations | | X | | |
| | SVC Ablations Only | | X | | |

TISSUE CONTACT SENSING WITH A MULTI ELECTRODE ABLATION CATHETER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for assessing electrode-tissue contact before the delivery of ablation energy.

BACKGROUND OF THE INVENTION

Many types of cardiac arrhythmia, conditions in which the heart's normal rhythm is disrupted, are often treated by ablation (for example, radio frequency (RF) ablation, cryoablation, ultrasound ablation, laser ablation, microwave ablation, and the like), either epicardially or endocardially. Cardiac ablation may be performed with a variety of devices, such as devices having expandable distal ends. For example, ablation of the tissue surrounding a pulmonary vein ostium may be performed with a device having a distal end that is expandable into a substantially circular configuration, such as the pulmonary vein ablation catheter (PVAC®, Medtronic, Inc., Minneapolis, Minn.).

However, the success of any cardiac ablation procedure depends largely on the quality of the lesion(s) created during the procedure. Lesion quality depends, in turn, on the quality of contact between the ablation electrodes and the target tissue. Anatomical variations within the pulmonary veins, or other areas of target tissue, may cause a loss of contact between one or more electrodes and the target tissue.

Currently known methods for assessing contact between an electrode and tissue include visual contact assessment using fluoroscopic imaging. However, this method requires costly imaging equipment and can be time consuming. Other methods of electrode-tissue contact assessment involve monitoring the temperature of and power delivered to each electrode, but such methods are typically used after the delivery of ablation energy has already begun and often do not prevent unintended tissue damage. Additionally, these methods can be ineffective and subject to wide variation between patients.

As noted above, ablation may be applied via catheters designed to deliver amount of energy that optimize therapy yet minimize damage to surrounding tissue. A catheter used to deliver electrical energy to tissue has an inherent capacity of relaying electrical information to a remote impedance measurement device. If an impedance measurement is made pre- and post-ablation, an accurate assessment can be made as to the quality of the lesion. Therefore, the catheter's utility may be extended beyond its single role of delivering ablation into that of a lesion gauge, negating the need to introduce other gauges, cameras, or imaging systems to perform the same functions.

Difficulties arise when attempting to make impedance measurements via catheters, especially those with a high electrode count (for example, 16-electrode catheters). For impedance measurements resolved by a catheter, it is necessary to discern a bipolar impedance existing between electrodes from a unipolar impedance existing from a single electrode to a neutral or patient return electrode. Currently known systems and methods do not perform impedance disambiguation, with no discernment between unipolar and bipolar impedance and separation of these from parasitic impedances for multi-electrode catheters. Thus, a physician cannot attribute an impedance rending to the catheter, let alone to a specific location corresponding to catheter electrodes. As a result, the physician cannot infer lesion quality. Therefore, in order to imply lesion quality, the catheter and the impedance measurement system must "untangle" the multitude of impedance elements so as to provide a clear indicator of a particular catheter electrode's physiological effect.

An important function must then be to sift and accurately resolve a multitude of unipolar and bipolar impedance elements resulting from the many circuitous pathways resulting from a multi-electrode catheter placed inside the heart. Beyond the desired unipolar and bipolar results that can be related to their respective electrodes, there are additional undesired parasitic pathways that act to corrupt the desired impedance renderings. These pathways must also be measured, and dissected, or de-embedded from the desired unipolar and bipolar readings automatically. Undesired parasitic pathways include catheter wire series impedance, electric field (capacitive) coupling between catheter wires, and the placement of signal splitters and filters in-line with the catheter that divert catheter sensed electrogram (EGM) signals for use by an electrocardiogram (ECG) monitor.

Because of the potentially long duration required to collect electrical information necessary to disambiguate, calculate, and report unipolar and bipolar impedance over a large set of catheter electrodes, the system must have the ability to perform impedance measurements rapidly. To enable rapid impedance measurements, the system must apply that energy across all catheter electrodes simultaneously so that measurement results are correlated in time across frequency and electrode so that results are unaffected by slight movements of the catheter against tissue within the heart. Additionally, the physician must have a function that automatically scales the impedance measurement system's detector gain while maintaining the catheter electrodes' delivered current at safe, yet maximum, levels while the physician traverses widely ranging tissue and fluid impedances. Widely disparate tissue impedance could occur due to the difference of blood and heart tissue, ablated vs. non-ablated tissue, as well as from ice that forms an electrically insulting barrier on the tip of a cryoablation catheter, assuming that an impedance measurement function is used to support cryoablation lesion quality assessment.

Patient safety is a paramount concern, and delivery of measurement energy must be low enough in amplitude so as to meet applicable standards and possess a waveform that is biphasic so that inadvertent stimulation of cardio or nerve tissue does not occur. A further important consideration for an impedance measurement system is to provide an automatic, traceable calibration conforming to applicable standards so that the instrument's impedance renderings are trustworthy.

Finally, since the physician may use the impedance measurement function to determine lesion quality (gauged by ablation impedance renderings) immediately prior to and after the moment of therapy, the impedance measurement system must remain connected in-line with the catheter and the ablation generator simultaneously. Therefore, some mechanism must sequence and protect the impedance measurement function during the delivery of the high energy therapy.

It is therefore desired to provide a method and system for accurate and reliable electrode-tissue contact assessment, and for electrode-tissue contact assessment before the delivery of ablation energy begins.

SUMMARY OF THE INVENTION

The present invention advantageously provides a method and system for assessing electrode-tissue contact before the delivery of ablation energy. In one embodiment, the system may include a medical device including a treatment assembly having a plurality of electrodes and a control unit in communication with the medical device, the control unit programmed to: determine a difference value between a maximum impedance magnitude at a low frequency for one of a plurality of electrodes and an absolute minimum impedance magnitude at the low frequency across all of the plurality of electrodes; determine a difference value between a maximum impedance magnitude at a high frequency for the one of the plurality of electrodes and an absolute minimum impedance magnitude at the high frequency across all of the plurality of electrodes; determine a difference value between a maximum impedance phase at the high frequency for the one of the plurality of electrodes and an absolute minimum impedance phase at the high frequency across all of the plurality of electrodes; correlate the difference values to each other for each of the plurality of electrodes; and assign to each of the plurality of electrodes a discrete prediction value based on the correlations. The low frequency may between approximately 5 kHz and approximately 15 kHz, such as 12.5 kHz, and the high frequency may be between approximately 80 kHz and approximately 140 kHz, such as 100 kHz. Correlating the differences to each other for each of the plurality of electrodes may include applying a linear model to the difference values. Further, each of the plurality of electrodes may be assigned a discrete prediction value that is either 0 or 1. For example, a discrete prediction value of 0 may be assigned to an electrode when the electrode is not in contact with tissue and a discrete prediction value of 1 may be assigned to an electrode when the electrode is in contact with the tissue. Further, a discrete prediction value of 2 may be assigned to an electrode when the electrode is in excessive contact with tissue. Ablation energy may be delivered to any of the plurality of electrodes to which a discrete prediction value of 1 is assigned.

In another embodiment, the system may include a medical device including a treatment assembly having a plurality of electrodes and a control unit in communication with the medical device, the control unit programmed to: record a impedance magnitude value at a first frequency by each of a plurality of electrodes and determine a maximum impedance magnitude value of the plurality of impedance magnitude values at the first frequency; record an impedance magnitude value at a second frequency by each of the plurality of electrodes and determine a maximum impedance magnitude value of the plurality of impedance magnitude values at the second frequency; record an impedance phase value at the second frequency by each of the plurality of electrodes and determine a maximum impedance phase value of the plurality of impedance phase values; record a minimum impedance magnitude value at the first frequency across all of the plurality of electrodes; record a minimum impedance magnitude value at the second frequency across all of the plurality of electrodes; recording a minimum impedance phase value at the second frequency across all of the plurality of electrodes; for each of the plurality of electrodes, calculate a first difference value between the maximum impedance magnitude value and the minimum impedance magnitude value recorded at the first frequency; for each of the plurality of electrodes, calculate a second difference value between the maximum impedance magnitude value and the minimum impedance magnitude value recorded at the second frequency; for each of the plurality of electrodes, calculate a third difference value between the maximum impedance phase value and the minimum impedance phase value recorded at the second frequency; and for each of the plurality of electrodes, apply a linear model to all of the first, second, and third difference values to determine a continuous prediction value for each of the plurality of electrodes. The system may further include a display in communication with the control unit. A continuous prediction value for each of the plurality of electrodes may be determined using the following equation: continuous prediction value=$a*1+b*\Delta Z_{100}+c*\Delta Z_{12.5}+d*\Delta\emptyset_{100}$. The control unit may be further programmed to assign a discrete prediction value to each of the plurality of electrodes based on a corresponding continuous prediction value, and the display may be configured to display at least one of the continuous prediction value for each of the plurality of electrodes and the discrete prediction value for each of the plurality of electrodes. The continuous prediction value and/or the discrete prediction value may be displayed in text, color, and/or graphical formats. For example, a graphical representation of the plurality of electrodes may be displayed, with each of the plurality of electrodes being displayed as a color that corresponds to at least one of the continuous prediction value and the discrete prediction value, the colors changing in real time with the at least one continuous prediction value and discrete prediction value. The second frequency may be higher than the first frequency. For example, the first frequency may be between approximately 5 kHz and approximately 15 kHz, such as 12.5 kHz, and the second frequency may be between approximately 80 kHz and approximately 140 kHz, such as 100 kHz. The continuous prediction value may be a number between 0 and 1. Further, a discrete prediction value of 0 may be assigned to a continuous prediction value that is less than a cutoff value and a discrete prediction value of 1 may be assigned to a continuous prediction value that is greater than or equal to the cutoff value. For example, the cutoff value may be 0.4 or 0.5. Further, the continuous prediction value may be a number that is equal to or greater than 0. A discrete prediction value of 0 may be assigned to a continuous prediction value that is less than a first cutoff value, a discrete prediction value of 1 may be assigned to a continuous prediction value that is greater than or equal to the first cutoff value and less than a second cutoff value, and a discrete prediction value of 2 may be assigned to a continuous prediction value that is greater than or equal to the second cutoff value. For example, the first cutoff value may be 0.4 and the second cutoff value may be 1.5

In another embodiment, the system may include a medical device including a treatment assembly having a plurality of electrodes and a control unit in communication with the medical device, the control unit programmed to: record a first maximum impedance magnitude value from each of a plurality of electrodes at 12.5 kHz; record a second maximum impedance magnitude value from each of the plurality of electrodes at 100 kHz; record a maximum impedance phase value from each of the plurality of electrodes at 100 kHz; record a first minimum impedance magnitude value across all electrodes of the plurality of electrodes at 12.5 kHz; record a second minimum impedance magnitude value across all electrodes of the plurality of electrodes at 100 kHz; record a minimum impedance phase value across all electrodes of the plurality of electrodes at 100 kHz; determine a difference value between the first maximum impedance magnitude value for each of the plurality of electrodes and the first minimum impedance magnitude value; determine a difference value between the second maximum impedance magnitude value for each of the plurality of electrodes and the second minimum impedance magnitude value; determine a difference value between the maximum impedance phase value for each of the plurality of electrodes and the minimum impedance phase value; apply a linear model to the difference values to determine a continuous prediction value between 0 and 1 for each of the plurality of electrodes; and assign a discrete prediction value of 0 to each of the plurality of electrodes for which the continuous prediction value is less than a cutoff value and assign a discrete prediction value of 1 to each of the plurality of electrodes for which the continuous prediction value is equal to or greater than the cutoff value. The system may further include a display in communication with the control unit, the display configured to display at least one of the continuous prediction value for each of the plurality of electrodes and the discrete prediction value for each of the plurality of electrodes in at least one of text, color, and graphical formats.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6 shows a grid for qualifying electrode-tissue contact determinations;

FIG. 7 shows a summary chart of factor analysis;

DETAILED DESCRIPTION OF THE INVENTION

Figure 1:
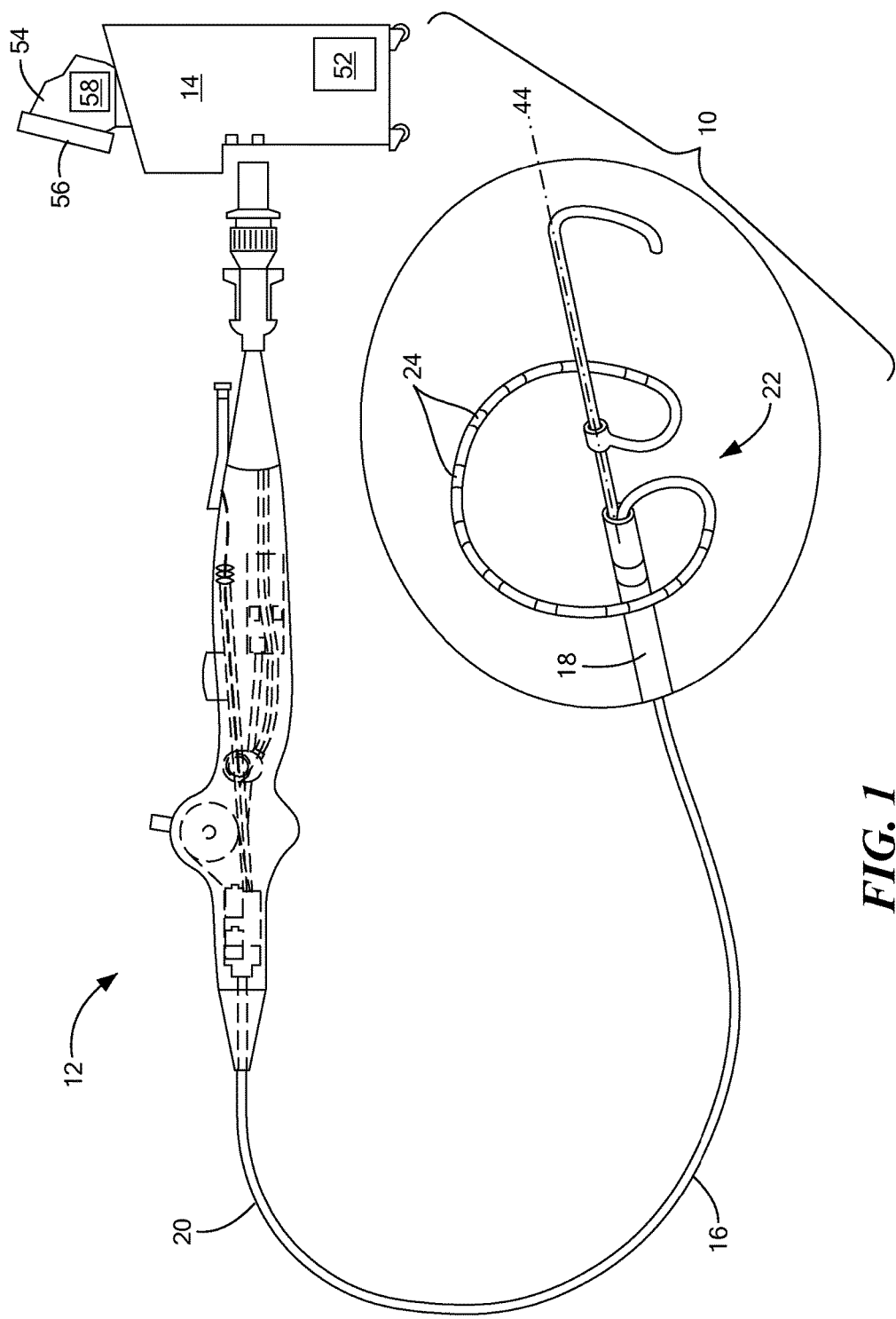
FIG. 1 shows an exemplary system for assessing electrode-tissue contact.
Figure 2A:
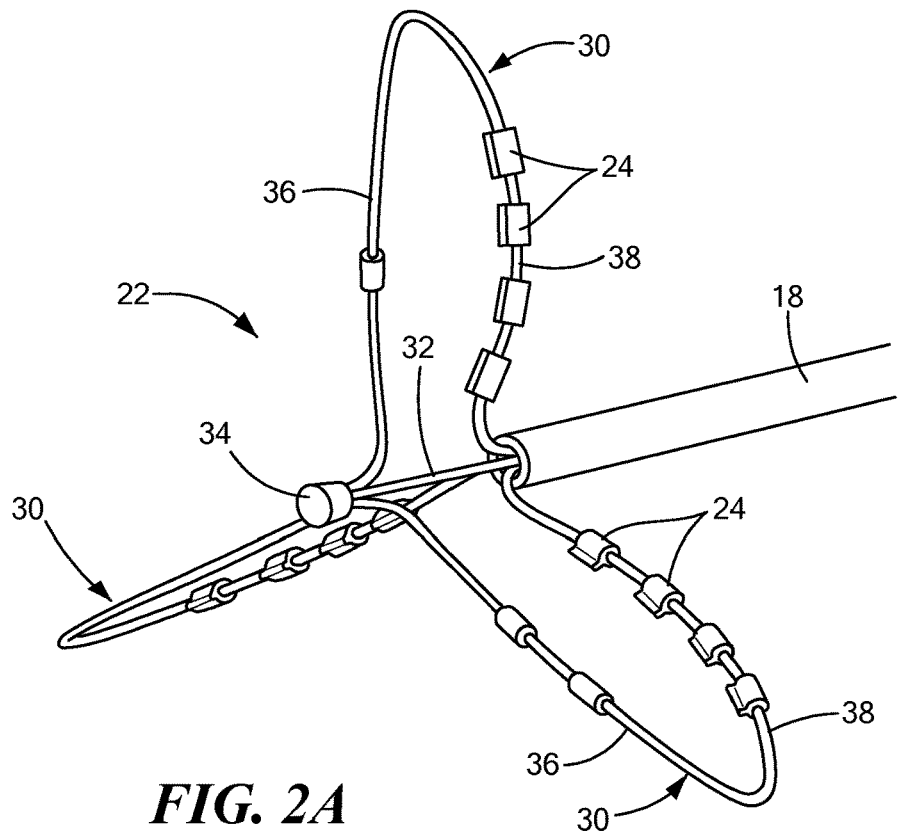
FIGS. 2A and 2B show exemplary distal portions of multi-electrode ablation catheters.
Figure 2B:
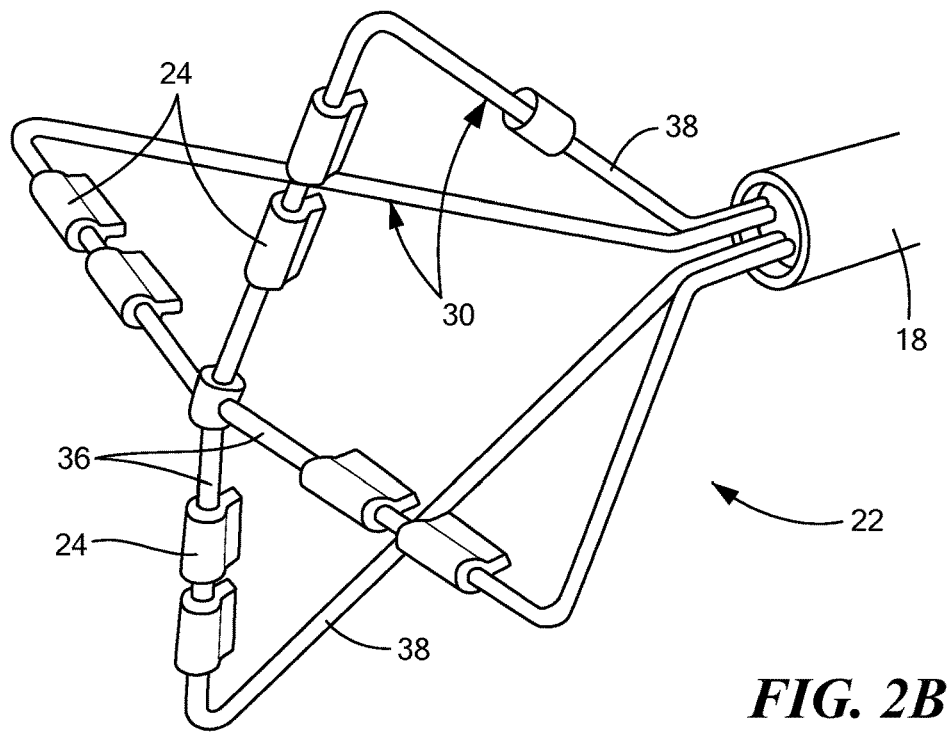
Figure 3:
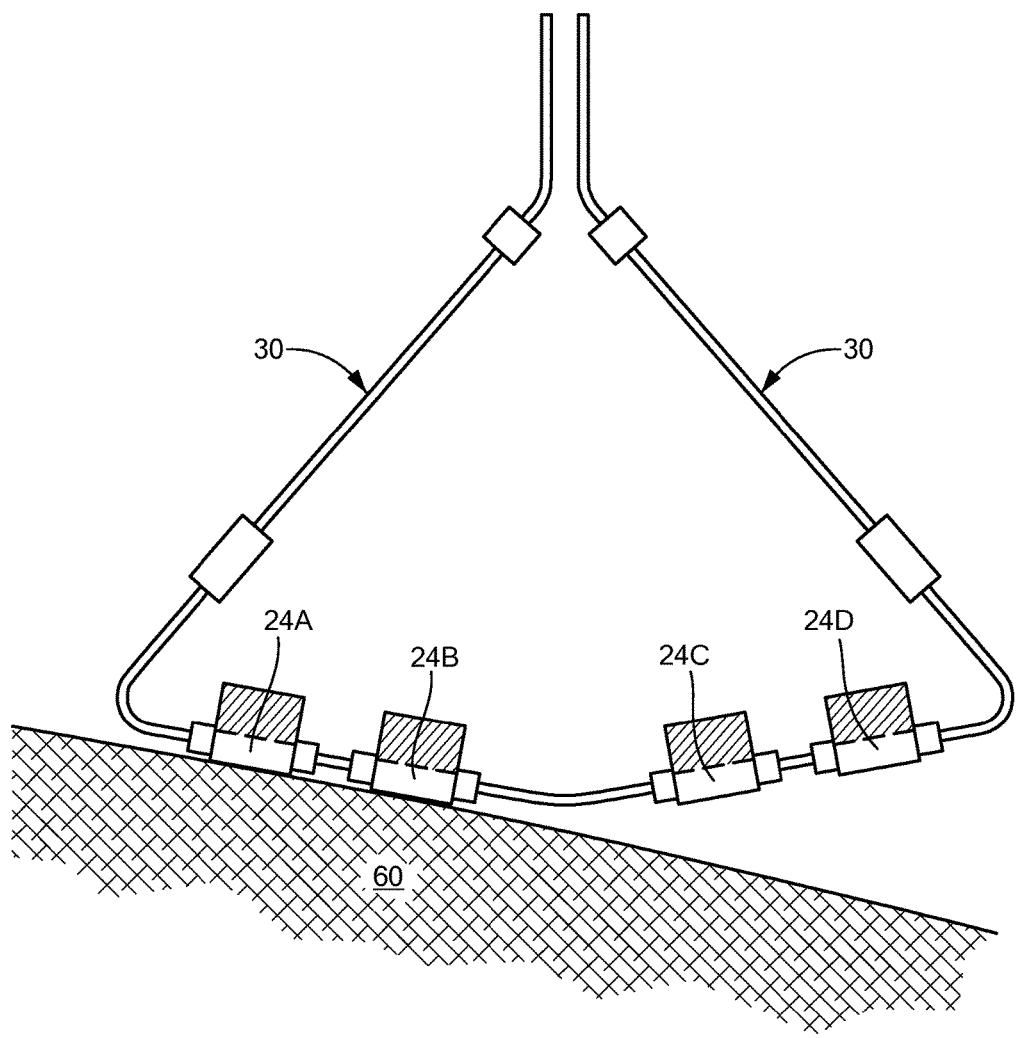
FIG. 3 shows a cross-sectional view of a treatment assembly of a multi-electrode ablation catheter in partial contact with target tissue.

Referring now to FIGS. 1-3, an exemplary system for assessing electrode-tissue contact is shown. The system 10 may generally include a treatment device, such as an ablation catheter 12, for thermally treating an area of tissue and a console 14 that houses various system controls. The system 10 may be adapted for the use of one or more energy modalities, such as radiofrequency (RF) ablation, cryoablation, electroporation, pulsed field ablation, and/or microwave ablation.

The ablation catheter 12 may include an elongate body 16 having a distal portion 18 and a proximal portion 20. The distal portion 18 may include a treatment assembly 22 with one or more ablation electrodes 24. For example, the treatment assembly 22 may include one or more carrier arms 30 each bearing one or more ablation electrodes 24. Although not shown, one or more of the carrier arms 30 may also bear one or more mapping electrodes, pacing electrodes, reference electrodes, radiopaque markers, sensors (such as temperature and/or pressure sensors), and/or other components.

Non-limiting examples of treatment assemblies are shown in FIGS. 1-3. As shown in FIG. 1, the treatment assembly 22 may include a shaft 32 slidably and rotatably movable within the elongate body and having a distal tip 34. The treatment assembly may also include a flexible carrier arm 30 having a distal portion 36 and a proximal portion 38, the distal portion 36 being coupled to the shaft distal tip 34 such that longitudinal movement and/or rotation of the shaft 32 within the elongate body 16 may adjust the configuration of the treatment assembly 22. For example, advancement of the shaft 32 distally may cause the treatment assembly 22 to have a linear or at least substantially linear configuration (not shown) that may be used for delivery of the device to the target site, whereas retraction of the shaft 32 may cause the carrier arm 30 to expand radially from the shaft 32 and assume an at least substantially circular configuration. Further, the diameter of the at least substantially circular configuration of the carrier arm 30 may be adjusted by rotation of the shaft 32 within the elongate body 16. The carrier arm 30 may bear a plurality of ablation electrodes 24 along its length. The device shown in FIG. 1 may be similar to the PVAC ablation catheter.

Alternatively, as shown in FIGS. 2A and 2B, the treatment assembly 22 may include more than one carrier arm 30. For example, the treatment assembly 22 may include three carrier arms 30 (as shown in FIG. 2A) or four carrier arms (as shown in FIG. 2B). The carrier arms 30 may be radially arranged about the longitudinal axis 44 of the ablation catheter, so as to create a symmetrical ablation pattern. Further, the treatment assembly 22 may include a shaft 32 with a distal tip 34, to which at least a portion of each carrier arm 30 is attached (as shown in FIG. 2A), with advancement and retraction of the shaft 32 transitioning the treatment assembly 22 between a linear or at least substantially linear configuration (not shown) for delivery of the device to the target site and an expanded treatment configuration (as shown in FIG. 2A). Alternatively, the carrier arms 30 may be coupled to each other without a shaft 32 (as shown in FIG. 2B).

The carrier arms 30 shown in FIG. 2A may each have a sagittate shape with the one or more ablation electrodes 24 being coupled to the proximal portion 46 of each carrier arm 30, so as to create a proximally oriented ablation plane or face. Conversely, the ablation electrodes 24 may be coupled to the distal portion 48 of each carrier arm 30, as shown in FIG. 2B, so as to create a distally oriented ablation plane or face. The device shown in FIGS. 2A and 2B may be similar to the multi-array septal catheter (MASCO, Medtronic, Inc., Minneapolis, Minn.) and the multi-array ablation catheter (MAAC®, Medtronic, Inc., Minneapolis, Minn.), respectively. However, it will be understood that other configurations other than those shown and described herein may be used, and that the treatment assembly may have any configuration, size, number of electrodes, number of carrier arms, and/or other features that render the treatment assembly suitable for ablating tissue. For example, a balloon catheter with electrodes on an outer surface of the balloon or a focal catheter may also be used.

The console 14 may generally include an energy source, such as a RF energy generator 52, one or more computers 54, and one or more other external components or internal components such as an impedance meter 55. The RF energy generator 52 may be in electrical communication with the one or more ablation electrodes 24. The one or more computers 54 may each include one or more displays 56, processors 58, and/or user input devices, and the one or more processors 58 also may be in electrical communication with the one or more ablation electrodes 24. One or more of the displays 56 and/or other user input devices may be wired to the console 14 or may be in wireless communication with the console 14. Optionally, the console 14 may also include one or more fluid reservoirs, valves, conduits, connectors, power sources, sensors, force gauges, navigation systems, displays, speakers, and the like for adjusting and monitoring system parameters and/or for generating one or more displays or alerts to notify the user of various system criteria or determinations.

When the multi-electrode treatment assembly 22 is placed proximate or at least partially in contact with an area of tissue, one or more of the electrodes 24 may be in contact with the tissue whereas one or more of the electrodes 24 may not. In the non-limiting example shown in FIG. 3, electrodes 23A and 24B are in contact with tissue whereas electrodes 24C and 24D are not. Being able to determine before initiating energy delivery which electrode(s) 24 are not in contact with the tissue may facilitate safer, more effective, and faster ablation procedures, as the user may be able to manipulate the catheter in real time to optimize contact between tissue and as many of the electrodes as possible. A method for assessing electrode-tissue contact is shown in the flowchart of FIGS. 4A-4D.

Referring now to FIGS. 4A-4D, the three main parameters of interest for this method are: (1) the difference between the maximum impedance magnitude at a low frequency (for example, 12.5 kHz) for a given electrode and the absolute minimum impedance magnitude at the same low frequency across all electrodes for that ablation; (2) the difference between the maximum impedance magnitude at a high frequency (for example, 100 kHz) for a given electrode and the absolute minimum impedance magnitude at the same high frequency across all electrodes for that ablation; and (3) the difference between the maximum impedance phase at a high frequency (for example, 100 kHz) for a given electrode and the absolute minimum impedance phase at the same high frequency across all electrodes for that ablation. This method uses relative values instead of absolute values for contact assessment. Additionally, this method involves normalizing the impedance magnitude and phase data by the corresponding minimum value recorded during the procedure instead of normalizing the impedance magnitude and phase data by the corresponding maximum value. Since the catheter must be in blood at some point during the procedure and impedance values in blood are lower than impedance values when recorded by electrodes in contact with tissue, the minimum impedance values correspond to when the catheter is in blood. The minimum impedance value may be affected by various blood characteristics, such as electrolyte, saline, and blood thinner levels. As determined experimentally, the average minimum (or "in blood") impedance value is approximately 100.45 with a standard deviation of approximately 11.38, with a maximum value being approximately 126.6 and a minimum value being approximately 85.5. The maximum impedance values may be obtained by sampling the impedance several times per second and "keeping" the maximum impedance value recorded over a one to two second window.

Figure 4A:
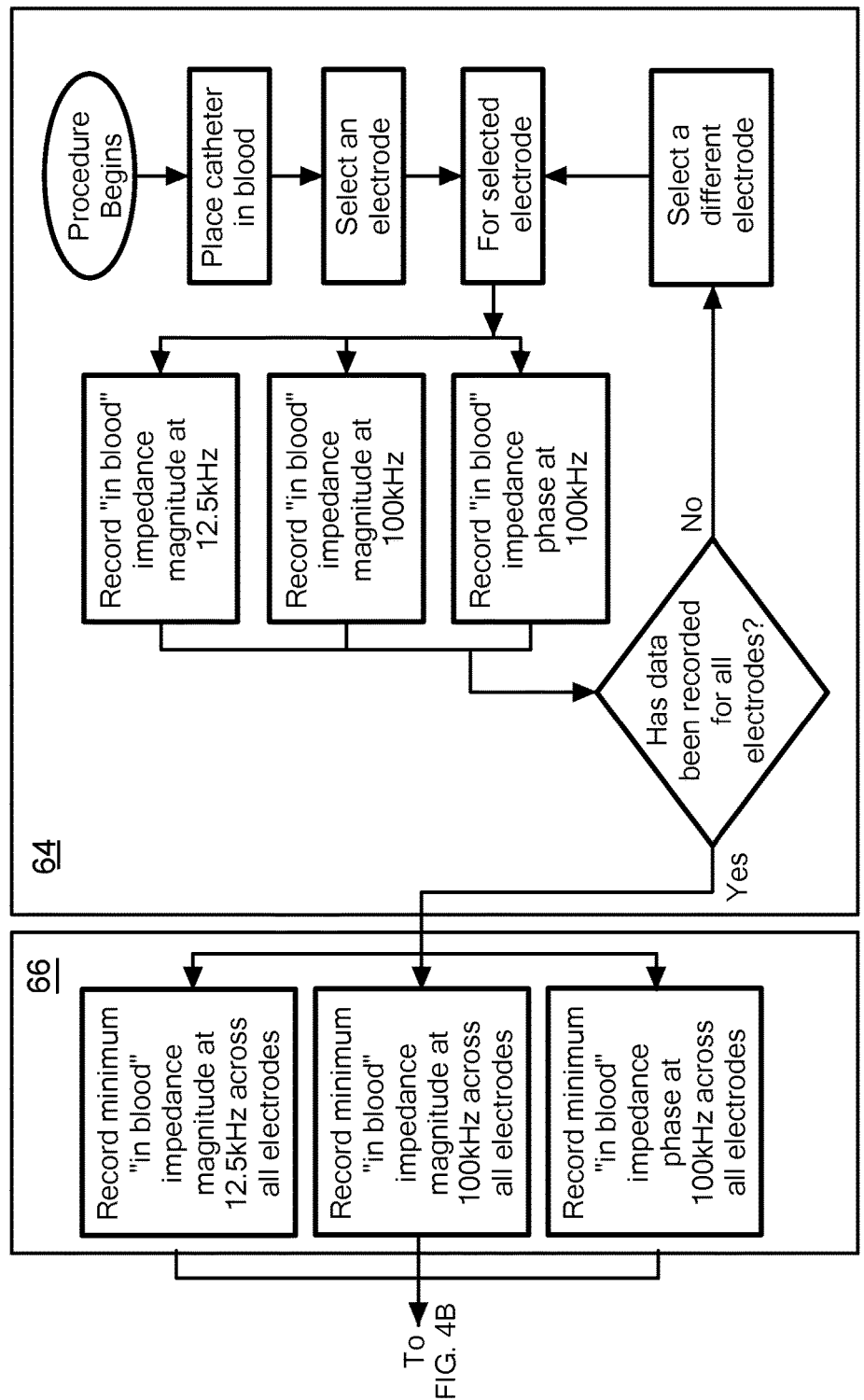
FIGS. 4A-4D show a flowchart for a method of assessing electrode-tissue contact.

In the first step 64, the treatment assembly 22 of the ablation catheter 12 may be positioned within the blood at a location near but not in contact with the target site. For example, if the target site is a pulmonary vein ostium, the treatment assembly 22 may be positioned within the blood in the left atrium of the patient's heart. For each electrode 24, three impedance measurements may be acquired. Further, these measurements may be acquired at a first low frequency and a second high frequency. As shown in FIG. 4A, a first impedance magnitude may be recorded at a low frequency (that is, a low-frequency current may be passed between two electrodes) and a second impedance magnitude may be recorded at a high frequency (that is, a high-frequency current may be passed between two electrodes) while the electrodes 24 are in blood and not in contact with tissue. As referred to throughout, the low frequency may be in the range of approximately 5 kHz to approximately 15 kHz (for example, 12.5 kHz) and the high frequency may be in the range of approximately 80 kHz to approximately 140 kHz (for example, 100 kHz). Finally, an impedance phase may be recorded at the same high frequency while the electrodes 24 are in blood and not in contact with tissue. These three measurements are recorded for each electrode 24, and although shown as being a sequential process in FIG. 4A, measurements may be taken from all electrodes simultaneously or sequentially. Additionally, the measurements at different frequencies may be taken sequentially simultaneously. Values may be measured and calculations may be updated every ⅛ second to 1 second. As a non-limiting example, impedance magnitude and phase may be measured simultaneously from pairs of electrodes, but the measurements from electrode pairs may be taken sequentially. Impedance values recorded at 12.5 kHz may measure extracellular fluid resistance, whereas impedance values recorded at 100 kHz may measure resistance of intracellular fluid and membranes.

In the second step 66 shown in FIG. 4A, a first minimum impedance magnitude may be recorded at a low frequency, such as 12.5 kHz, across all electrodes 24 and a second minimum impedance magnitude may be recorded at a high frequency, such as 100 kHz, across all electrodes 24 while the electrodes 24 are still in blood and not in contact with tissue. Finally, an impedance phase may be recorded at the same high frequency (100 kHz) across all electrodes 24 while the electrodes 24 are still in blood and not in contact with tissue. For example, the system may continuously record impedance magnitude values when the low frequency energy is delivered and may continuous record impedance magnitude and phase values when the high frequency energy is delivered. The one or more processors 58 may store a minimum magnitude value at the low frequency, a minimum magnitude value at the high frequency, and a minimum phase value at the high frequency. If a new minimum value is recorded for any of the values of interest, the new minimum value replaces the previous minimum value as the stored minimum value. Further, the minimum value may be a single discrete value or it may be the average or median of a plurality of minimum values in order to remove outlier values.

Figure 4B:
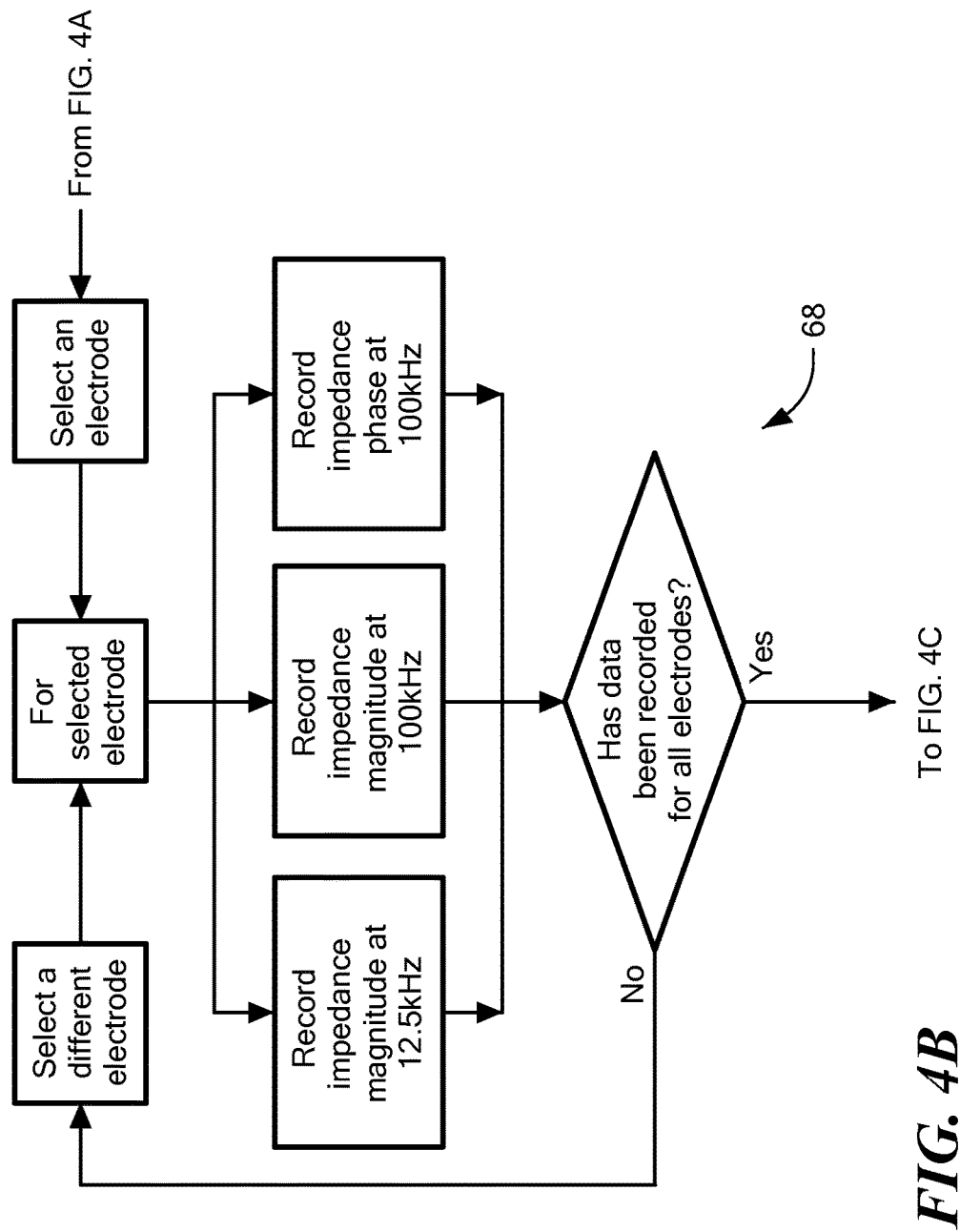

In the third step 68 shown in FIG. 4B, the treatment assembly 22 may be positioned so that it is at least partially in contact with an area of tissue (for example, the target tissue). Once the treatment assembly 22 is at least partially in contact with the target tissue, three more measurements may be taken for each electrode 24. Alternatively, measurements may be continually measured while positioning the treatment assembly 22 (and updated every ⅛ second to 1 second) to assist in the placement of the treatment assembly 22 in contact with tissue. A first impedance magnitude may be recorded at a low frequency, such as 12.5 kHz, and a second impedance magnitude may be recorded at a high frequency, such as 100 kHz, while the treatment assembly 22 is at least partially in contact with tissue. Finally, an impedance phase may be recorded at the same high frequency (100 kHz) while the electrodes 24 are in blood and not in contact with tissue. These three measurements are recorded for each electrode 24, and although shown as being a sequential process in FIG. 4B, measurements may be taken from all electrodes simultaneously or sequentially.

Figure 4C:
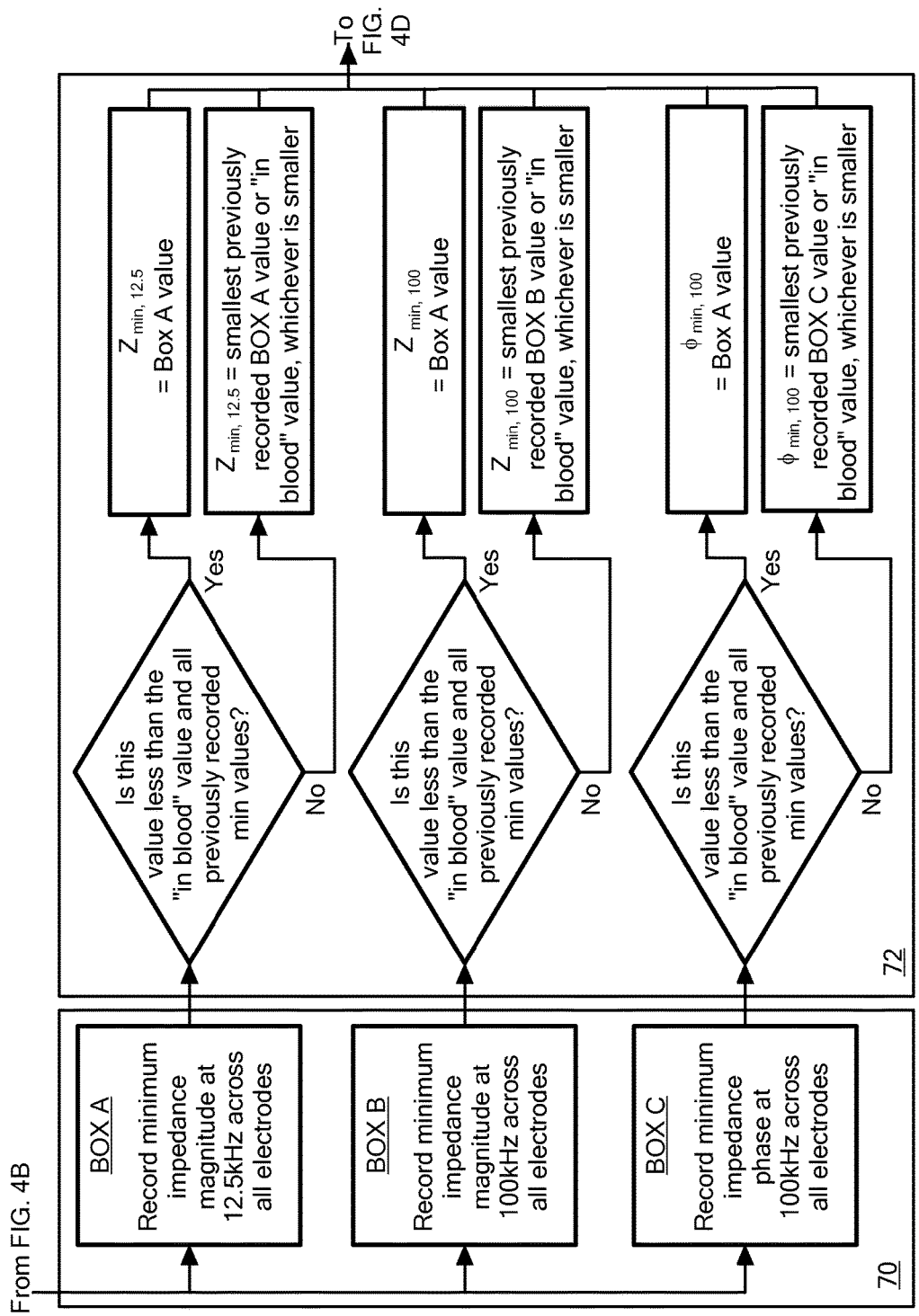

In the fourth step 70 shown in FIG. 4C, a first minimum impedance magnitude may be recorded at a low frequency, such as 12.5 kHz, across all electrodes 24 and a second minimum impedance magnitude may be recorded at a high frequency, such as 100 kHz, across all electrodes 24 while the treatment assembly 22 is at least partially in contact with tissue. Finally, an impedance phase may be recorded at the same high frequency (100 kHz) across all electrodes 24 while the treatment assembly 22 is at least partially in contact with tissue.

In the fifth step 72 shown in FIG. 4C, each of the measurements recorded in the fourth step 70 may be compared to the measurements taken in the first 64, second 66, and third 68 steps. For example, it may be determined whether the minimum impedance magnitude recorded at the low frequency (12.5 kHz) across all electrodes in the fourth step 70 is less than the "in blood" impedance magnitudes of each electrode 24 (of the first step 64) and all previously recorded minimum impedance magnitudes (in the second step 66). This determination may be referred to as "Box A." Further, it may be determined whether the minimum impedance magnitude recorded at the high frequency (100 kHz) across all electrodes in the fourth step 70 is less than the "in blood" impedance magnitudes of each electrode 24 (of the first step 64) and all previously recorded minimum impedance magnitudes (in the second step 66). This determination may be referred to as "Box B." If the answer to the Box A determination is "yes," the Box A value is the minimum impedance magnitude recorded at 12.5 kHz, or $Z_{min,12.5}$. If the answer to the Box A determination is "no," the Box A value is the smallest previously recorded Box A value or "in blood" value, whichever is smaller. Likewise, if the answer to the Box B determination is "yes," the Box B value is the minimum impedance magnitude recorded at 100 kHz, or $Z_{min,100}$. If the answer to the Box B determination is "no," the Box B value is the smallest previously recorded Box B value or "in blood" value, whichever is smaller.

Additionally, it may be determined whether the minimum impedance phase recorded at the same high frequency (100 kHz) across all electrodes in the fourth step 70 is less than the "in blood" impedance phase of each electrode 24 (of the first step 64) and all previously recorded minimum impedance magnitudes (in the second step 66). This determination may be referred to as "Box C." If the answer to the Box C determination is "yes," the Box C value is the minimum impedance phase recorded at 100 kHz, or $\emptyset_{min,100}$. If the answer to the Box C determination is "no," the Box C value is the smallest previously recorded Box C value or "in blood" value, whichever is smaller.

Figure 4D:
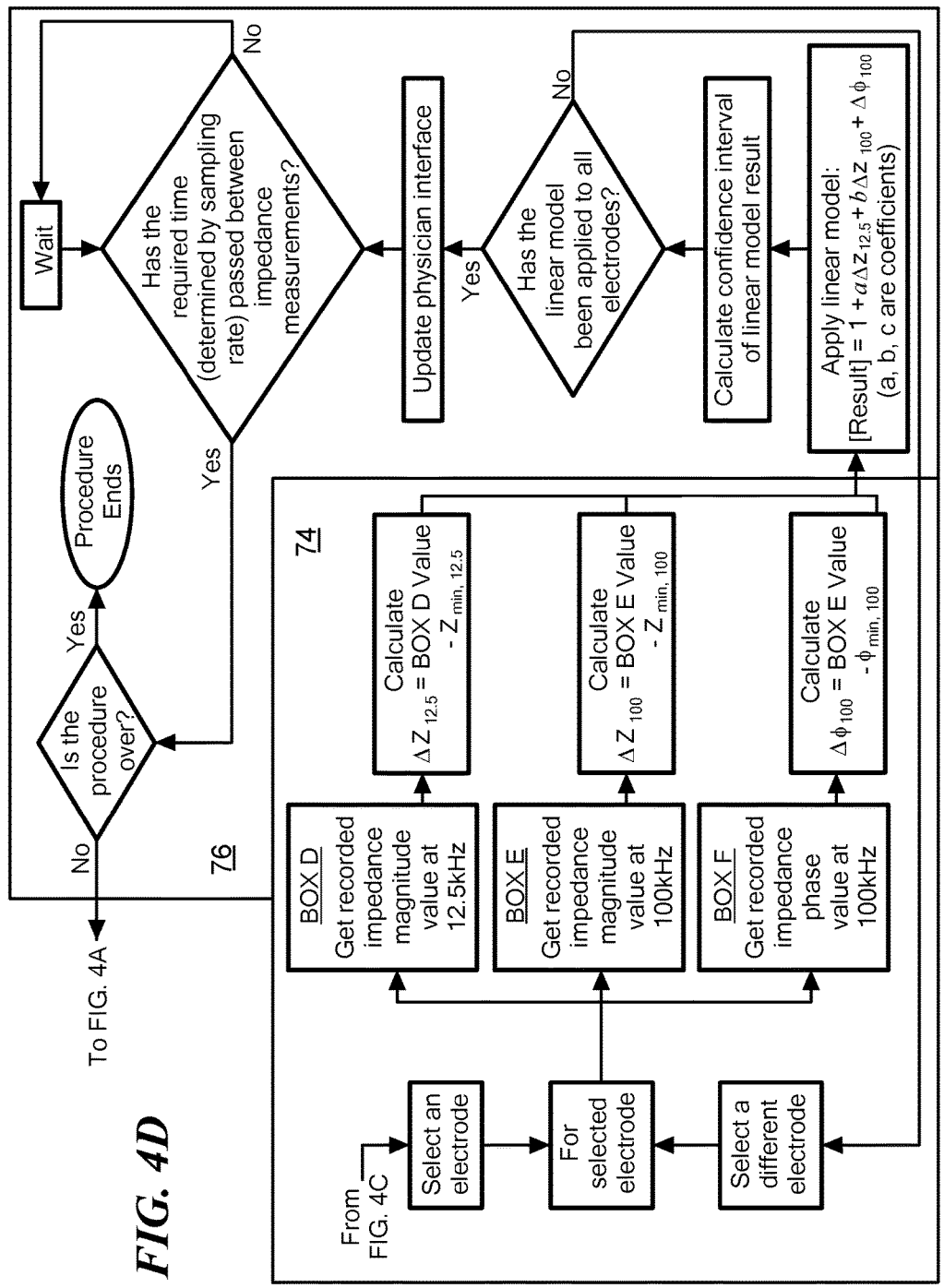

In the sixth step 74 shown in FIG. 4D, the impedance magnitude recorded in the third step 68 at the low frequency (12.5 kHz) for each electrode 24 may be referred to as "Box D," the impedance magnitude recorded in the third step 68 at the high frequency (100 kHz) for each electrode 24 may be referred to as "Box E," and the impedance phase recorded in the third step 68 at the same high frequency (100 kHz) for each electrode 24 may be referred to as "Box F." The change in impedance magnitude may be calculated for each of Boxes D and E and the change in impedance phase may be calculated for Box F. For example, the difference in impedance magnitude at the low frequency (12.5 kHz) may be the Box D value and the minimum impedance recorded at the low frequency (12.5 kHz) in Box A (as shown in Equation (1) below), the difference in impedance magnitude at the high frequency (100 kHz) may be the Box E value and the minimum impedance recorded at the high frequency (100 kHz) in Box B (as shown in Equation (2) below), and the difference in impedance phase at the high frequency (100 kHz) may be the Box F value and the minimum impedance phase recoded at the high frequency (100 kHz) in Box C, as shown in Equation (3) below:

$$\Delta Z_{12.5} = \text{BOX } D \text{ Value} - Z_{min,12.5} \quad (1)$$

$$\Delta Z_{100} = \text{BOX } E \text{ Value} - Z_{min,100} \quad (2)$$

$$\Delta \emptyset_{100} = \text{BOX } F \text{ Value} - \emptyset_{min,100} \quad (3)$$

In the seventh step 76 shown in FIG. 4D, a linear model may be applied for each electrode 24 according to Equation (4) below:

$$[\text{Result}] = a*1 + b*\Delta Z_{100} + c*\Delta Z_{12.5} + d*\Delta \emptyset_{100} \quad (4)$$

with "a," "b," "c," and "d" being coefficients (for example, the coefficients "a," "b," "c," and "d" may be based on clinical data). The result is a continuous number (which may be referred to herein as a "continuous prediction value") that may then be compared to a cutoff value to determine whether the electrode-tissue contact status is "no contact" (and therefore assigned a value of 0) or "good contact" (and therefore assigned a value of 1). To fit the linear model to the data, the status of "contact" may be given a value of 1 and a status of "no contact" may be given a value of 0. Then, the coefficients may be calculated that best fit the development data. For example, analysis of the development data may determine the values of coefficients "a", "b", "c", and "d" that best fit the model to predict contact (1) or no contact (0). The ΔZ values may be calculated by subtracting the current Z value from the minimum measured Z value. The Z value may be either the magnitude of the impedance or the real component of the impedance. The phase value may be either in the form of the phase in degrees or the imaginary component of the impedance. Additionally, A status of "contact," regardless of the type of contact, may be grouped together. For example, an electrode may have a status of "contact" when the electrode in optimal contact with tissue and when the electrode is in excessive contact with the tissue (such as when the electrode is buried in the tissue). In addition to a value of "contact" or "no contact," However, the model may be further developed to give a continuous result value between 0 and 2, in which case the contact status identification could be expanded to include "no contact," "contact," or "excessive contact." The coefficients may be calculated in the same way as discussed above for the "contact"/"no contact" evaluation. As a non-limiting example, the electrode-tissue contact status may be determined to be "no contact" when the continuous prediction value is less than or equal to a first cutoff value (for example, 0.4 or 0.5), "contact" when the continuous prediction value is greater than the first cutoff value but less than or equal to a second cutoff value (for example, 1.5), and "excessive contact" when the continuous prediction value is greater than the second cutoff value. Further, a status of "no contact" may be assigned a discrete prediction value of 0, a status of "contact" may be assigned a discrete prediction value of 1, and a status of "excessive contact" may be assigned a discrete prediction value of 2.

Still further, it will be understood that the model may be further developed to include more than three contact status categories. As a non-limiting example, the model may be developed to provide for determinations of "no contact" (for example, a continuous prediction value less than or equal to a first cutoff value), "previously ablated tissue" (for example, a continuous prediction value greater than the first cutoff value but less than or equal to a second cutoff value), "contact" (for example, a continuous prediction value greater than the second cutoff value but less than or equal to a third cutoff value), and "excessive contact (for example, a continuous prediction value greater than the third cutoff value but greater than or equal to a fourth cutoff value). In this case, a status of "no contact" may be assigned a discrete prediction value of 0, a status of "previously ablated tissue" may be assigned a discrete prediction value of 1, a status of "contact" may be assigned a discrete prediction value of 2, and a status of "excessive contact" may be assigned a discrete prediction value of 3.

The confidence interval of the linear model results may then be calculated and then displayed to the user. For example, the system may have collected enough data for the algorithm to return results with a 95% confidence interval. However, higher or lower confidence intervals may also be displayed, based on the amount of measurements collected. In addition to or instead of displaying the discrete 0 or 1 (or 2, 3, etc.) result to the user, the linear prediction continuous result (that continuous prediction value) may be displayed to the user in real time. Displaying the continuous result value may be useful, for example, to assess a state of intermittent contact for one or more electrodes, and to evaluate contact continuously during electrode placement and the treatment procedure. Values may be displayed to the user as text, in bar or other graphical formats, in a continuously changing linear display, by color, or other means. As a non-limiting example, a graphical representation of the treatment assembly 22 with one or more electrodes 24 may be displayed to the user. As the treatment assembly 22 is positioned or repositioned at or proximate a target tissue site, a numerical value, graphical depiction, color value, or other characteristic associated with each electrode 24 may change in real time so the user can easily visualize the changes in contact status of each electrode. For example, the color of each area o of the graphical representation corresponding to an electrode 24 may change color in real time, with red representing a status of "no contact" or "excessive contact" and green representing a status of "contact." Further, as a continuous prediction value approaches a cutoff value, the color associated with that electrode may change to a color on the spectrum between the color associated with the color of the next cutoff value. Alternatively, discrete or continuous prediction values may be presented to the user in a graphical representation of a gauge, with a needle moving between values. Although the system 10 may display to the user a status of "contact" or "no contact" (or other status, such as "excessive contact") in text based on the algorithm results discussed above, the system may additionally or alternatively display a numerical result to the user and the user can then determine, for example, when contact is sufficient or excessive without relying on the system's determination. Still further, the system 10 may automatically deactivate or turn off, or display a suggestion to the user that one or more electrodes be deactivated or turned off, if the contact status for those one or more electrodes is, for example, "no contact," "intermittent contact," or "excessive contact." Similarly, the system 10 may automatically (or prompt a user input to) extend the ablation time for one or more electrodes if the system 10 determines that those one or more electrodes have intermittent contact with the target tissue. It will be understood that the data discussed herein, including continuous prediction values and discrete prediction values, may be presented to the user in any of a variety of ways.

If the required time has elapsed between impedance measurements and the procedure is considered to be over, the procedure ends (for example, by ceasing delivery of ablation energy to the electrodes 24). If the required time has elapsed between the impedance measurements has elapsed but the procedure is not considered to be over, the method may be repeated from the third step 68 shown in FIG. 4B. The method of assessing electrode-tissue contact disclosed herein may be used throughout a procedure, between periods of delivery of ablation energy. During periods of ablation energy delivery, parameters such as temperature and power may be used to assess electrode-tissue contact. Further, ablation energy may be delivered to any of the electrodes 24 that are determined to be in contact with an area of target tissue and/or the treatment assembly 22 may be repositioned until more or all of the electrodes 24 are in contact with the area of target tissue.

Although the method includes recording impedance measurements before and after electrode contact with tissue, impedance measurements are continuously recorded in real time as the catheter is being positioned. For example, when the electrodes are located in the blood and not in contact with tissue, this contact status will be communicated in real time to the user. Additionally or alternatively, recoded impedance values may be communicated in real time to the user without previous contact status interpretation. As the electrodes come into contact with tissue, the impedance measurements for some or all of the electrodes may change, which will also be communicated to the user in real time as contact is established. As a non-limiting example, impedance measurements may be recorded from each electrode multiple times per second (for example, approximately eight times per second) and then averaged for display to the user. Additionally, impedance measurements (phase and magnitude) may be recorded for both the high and low frequencies simultaneously.

Exemplary Test Data

An initial pool of 180 data points was collected. Each data point was from one electrode of a nine-electrode treatment assembly over 20 ablation procedures. In order to normalize the measurements, a minimum impedance magnitude and minimum impedance phase were measured from an electrode that was confirmed to not be touching tissue (that is, the electrode was located within the left atrium, away from the atrial walls). Each electrode was then assigned a value of 0 ("no contact") or 1 ("good contact"). As an electrode temperature will not increase during ablation when the electrode is not in contact with tissue because of the cooling effect of surrounding blood flow, temperature measurements obtained during ablation were used as an adjudication method. MATLAB was used to fit a least-squares regression curve using the assigned contact state of each electrode as a discrete response variable and the normalized impedance measurements were used as continuous prediction values. Several polynomial models were used as regression curve-fitting methods to determine effects on algorithm performance. Further, the least-squares fit result (a continuous value between 0 and 1) was rounded to the nearest integer (0 or 1) to determine the algorithm's contact result (that is, "no contact" or "good contact"). If the algorithm result was greater than or equal to the cutoff value, the result was rounded to 1. Conversely, if the algorithm result was less than the cutoff value, the result was rounded to 0. Additional contact status qualifiers may be used, such as "excessive contact" and "previously ablated tissue," as discussed above. In such cases, additional cutoff values may be used. Decreasing the cutoff value raised the algorithm's sensitivity and may lower the specificity due to a probable increase in the number of false positives and decreased in the number of false negatives. Increasing the cutoff value had the opposite effect. For example, it was determined that a cutoff value of 0.4 was better at identifying when electrodes were in good contact with tissue, whereas an algorithm with a cutoff value of 0.5 was better at identifying when electrodes were not in contact with tissue. In practice, however, the cutoff value may be set according to user preferences with respect to high/low sensitivity and specificity.

The 180 data points were then separated into two groups: a development group including 120 selected data points of the 180 initial data points used to develop the algorithm, and a test group including the remaining 60 data points of the 180 initial data points, to which test group the algorithm was applied. The 120 selected data points included approximately two-thirds of the data points defined as "no contact" (that is, a having a value of 0) and approximately two-thirds of the data points defined as "good contact/low power" (that is, having a value of 1). The remaining approximately one-third of the data points defined as "no contact" and approximately one-third of the data points defined as "good contact/low power" were included in the test group. The development group data were used to develop and fine-tune the prediction method, whereas the performance of the prediction method was tested on the test group data.

For the development group, the three main parameters of interest (discussed regarding FIGS. 4A-4D) were used to determine the optimum linear combination using the MATLAB® (The Mathworks, Inc., Natick, Mass.) function "fitlm" (least squares fit of the response to the data). Multiple linear combination methods were used. The response variable of the linear combination was the group number (0 for "no contact" and 1 for "good contact"). Since the input variables were continuous but the response variables were discrete, the result from the linear combination was rounded to the nearest integer. The rounded result from the linear combination was then compared with the expected result (the group number determined from inspection of the plots and mean temperature and power data).

To assess algorithm performance, the sensitivity, specificity and positive predict values (PPV) for each curve-fitting method were calculated using the following equations:

Sensitivity=Number of True Positives÷(Number of True Positives+Number of False Negatives) (5)

Specificity=Number of True Negatives÷(Number of True Negatives+Number of False Positives) (6)

Positive Predictive Value=Number of True Positives÷(Number of True Positives+Number of False Positives) (7)

Negative Predictive Value=Number of True Negatives÷(Number of True Negatives+Number of False Negatives) (8)

As shown in FIG. 6, the term "True Positive" used above refers to a case in which the algorithm assigns "good contact" when the electrode really is in contact with tissue. The term "True Negative" used above refers to a case in which the algorithm assigns "no contact" when the electrode really is not touching tissue. The term "False Positive" used above refers to a case in which the algorithm assigns "good contact" when the electrode really is not touching tissue. Finally, the term "False Negative" used above refers to a case in which the algorithm assigns "no contact" when the electrode really is in contact with tissue.

For the test group, the same three main parameters of interest (discussed regarding FIGS. 4A-4D) were used to determine the optimum linear combination. Linear combinations created from the development group data were applied to the test group data. The response variable of the linear combination was the group number (0 for "no contact," 1 for "good contact"). Again, since the input variables were continuous but the response variable was discrete, the result from the linear combination was rounded to the nearest integer. The rounded result from the linear combination was then compared with the expected result (the group number determined from inspection of the plots and mean temperature and power data). The sensitivity, specificity, positive prediction value, and negative prediction value were calculated for each linear combination method.

The linear models used in both the development group and the test group were the linear model (linear terms for each predictor), interactions model (products of pairs of predictors with no squared terms), pure quadratic model (linear terms and squared terms), quadratic (product terms and squared terms), and polyijk model (polynomial with all terms up to degree I in the first predictor, degree j in the second predictor, etc.). All of these models are basic linear models available for use in MATLAB, and experimental data showed that the linear model type does not significantly impact the statistical results. The simplest curve-fitting method, a linear method, achieved performance comparable with more complex methods. The linear method algorithm achieved a sensitivity of 93%, a specificity of 85%, and a PPV of 92% for the development group and a sensitivity of 97%, a specificity of 90%, and a PPV of 92% for the test group.

Using pre-ablation predictors to create the algorithm may be more sensitive than using post-ablation predictors. Further, using only pre-ablation predictors may be better than using a combination of pre-ablation predictors and post-ablation predictors. However, this method and algorithm still performs well on previously ablated tissue. The algorithm may be used to distinguish between unablated tissue, previously ablated tissue, and no contact. For example, a lower continuous prediction value may indicate no contact, a higher continuous prediction value may indicate previously ablated tissue, and a high continuous prediction value may indicate unablated tissue.

Two data adjudication methods were used to determine if each electrode in the data set was in good contact with tissue or not in contact with tissue: (1) temperature-power method used to adjudicate non-superior vena cava (non-SVC) ablations, and (2) histology to adjudicate SVC ablations. In the first method, temperature and power measurements were used to determine electrode-tissue contact based on the conditions described in Table 1.

TABLE 1

Assessment of electrode contact.

| Category | Mean Temperature (° C.) | Mean Power (W) |
|---|---|---|
| Good Contact | ≥47 | ≥3 |
| Low Power | ≥47 | <3 |
| No Contact | <47 | N/A |

Figure 5A:
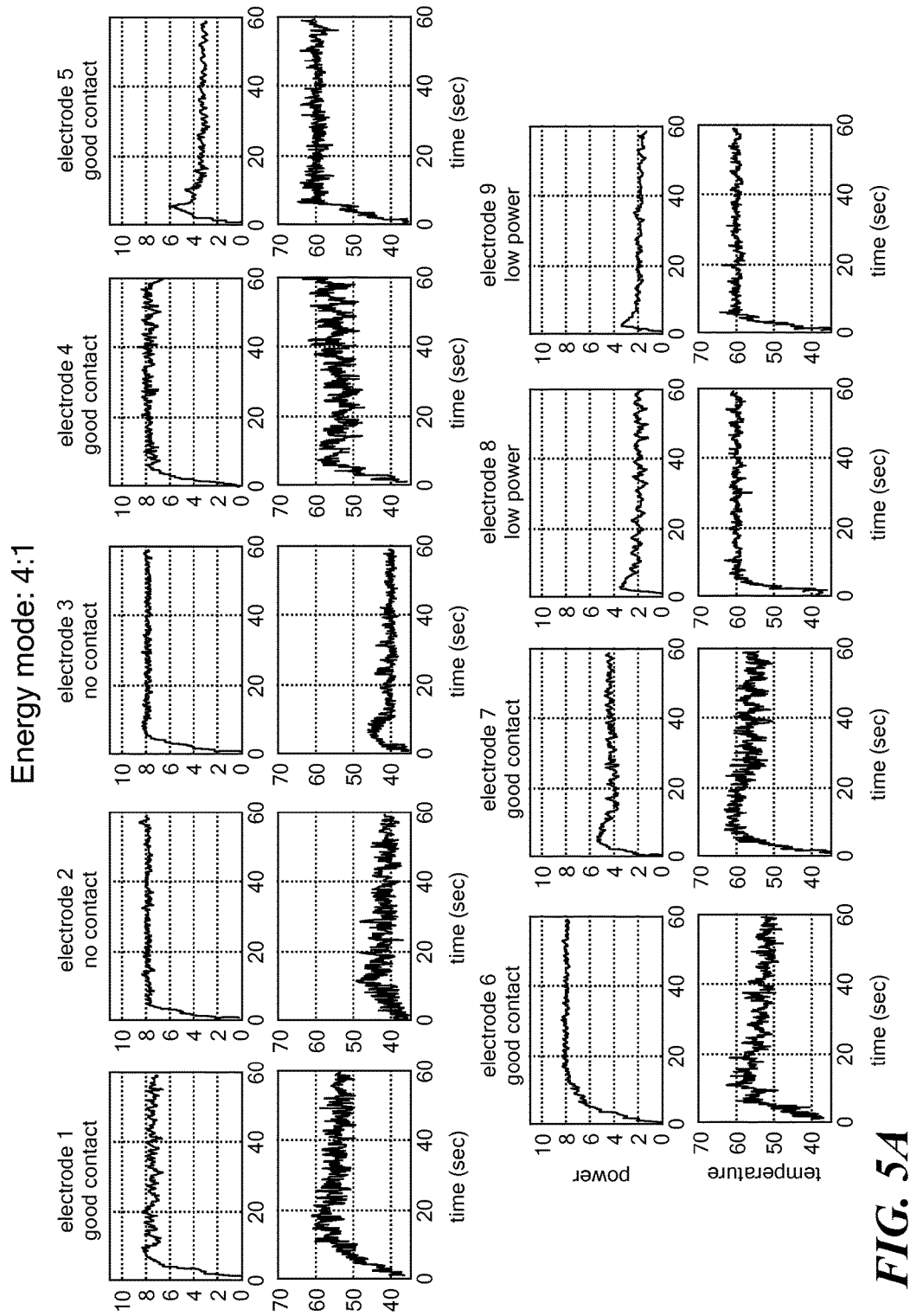
FIGS. 5A and 5B show exemplary power and temperature measurements.
Figure 5B:
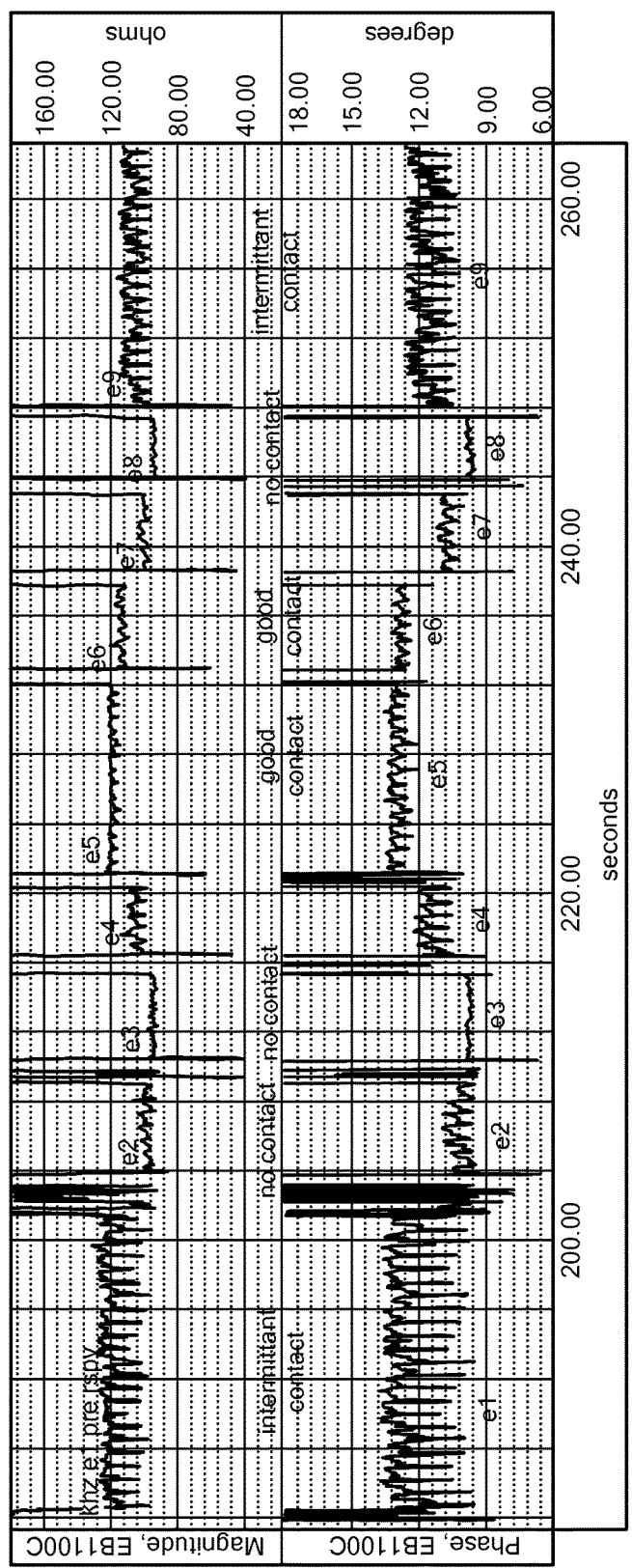

Electrodes in the "low power" category were defined to be in good tissue contact. However, if the third electrode-tissue contact qualifier "excessive contact" is used, the "low power" results may be considered to be indicated of excessive contact between an electrode and tissue. A non-limiting example of temperature and power measurements is shown in FIGS. 5A and 5B. FIG. 5A shows examples of "no contact," "good contact," and "low power," whereas FIG. 5B shows examples of "no contact," "good contact," and "intermittent contact." Intermittent contact may be indicated by impedance values that fluctuate between low impedance values and high impedance values (as shown for electrodes 1, 4, 7, and 9 in FIG. 5B).

In the second method, histology was examined following an ablation procedure. Histology data was available from chronic porcine studies. All ablations performed in the chronic studies were superior vena cava (SVC) ablations. All SVC ablations were assigned either "good contact" or "no contact" based on the histology results for each electrode. It was determined that there was no significant difference in algorithm performance when an algorithm developed using a data set containing data adjudicated using both methods was applied to a test group versus a test group containing only histology-adjudicated data. Therefore, the robustness of the temperature-power adjudication method is comparable to the robustness of the histology adjudication method.

It was determined that algorithm performance was dependent upon the composition of the data set used to develop it. Using impedance data from SVC ablations where there was good contact and impedance data from when the catheter was in blood from non-SVC ablations yielded superior algorithm performance compared to when SVC and non-SVC ablations were used. This may be because there was a clear separation between the "good contact" and "no contact" groups and the grey area was almost completely eliminated. However, it was also determined that the composition of the test group data set did not significantly impact algorithm results. The results obtained when the test group was comprised of only SVC ablations was comparable to when the test group was comprised of both SVC and non-SVC ablations. These findings are summarized in the chart shown in FIG. 7.

Although not expressly discussed herein, it will be understood that the algorithm may also be adapted to accurately recognize when an electrode is in contact with previously ablated tissue and indicate contact in a more continuous scale (for example, to indicate when there is a likelihood of good contact or excessive contact). Further, it will be understood that at least one processor 58 may include the algorithm (that is, may perform calculations using the algorithm) based on measurements received from the one or more electrodes 24 and/or from other system components. The processor 58 may then communicate the results of the calculations to the user via the one or more displays 56 or other system components.

Exemplary System Configuration

The device, system, and method disclosed herein may be specifically used to assess electrode-tissue contact using impedance measurements. However, the device, system, and method may also generally be used to provide intracardiac multi-frequency, multi-electrode impedance measurements for other purposes. Given an N-electrode catheter, a method and system is provided for resolving 2N total impedance elements: N bipolar and N unipolar impedance elements, which result from the application of an N-electrode catheter in contact with blood, pre-ablation cardiac tissue, post-ablation cardiac tissue, or ice formation on a cryoablation catheter. The method and system may maximize a catheter delivered current that is consistent with applicable patient safety standards and may minimize the risk of inadvertent cardiac or nerve stimulation by eliminating unipolar charge delivery. Further, the method and system may distribute signals to the catheter electrodes via a 2N switch array system. These functions may be performed while delivering a multi-spectral, simultaneous measurement current that allows for the simultaneous measurement and resolution of unipolar and bipolar impedances.

The method and system may also be used for: (a) the measurement, detection, and resolution of cathode-delivered multi-spectral, simultaneous measurement currents into their mono-frequency constituents; (b) the disambiguation of unipolar and bipolar impedances from parasitic pathway impedances resulting from non-ideal catheter delivery wire impedance, inter-catheter wire field coupling mechanisms, and ablation delivery system signal splitter and filter conductive pathways and field coupling mechanisms; (c) the adaptation of wide-ranging voltage and current measurements resulting from similarly wide-ranged values of blood, pre-ablation cardiac tissue, post-ablation cardiac tissue, or ice formation on a cryoablation catheter; (d) a method of calibration of the impedance renderings that provides surety to traceable international standards; and (e) the connection and synchronization of the impedance measurement apparatus to a radiofrequency or pulsed field ablation generator 52.

Referring now to FIGS. 8-17, the particulars of an exemplary system for, generally, rendering alternating current impedances from a set of ablation catheter electrodes in contact with tissue and bodily fluid and for, specifically, the assessment of electrode-tissue contact, are shown. The ablation catheter 12 having one or more electrodes 24 (as shown and described above) may be organized as a matrix of electrical nodes and bipolar impedances that reside between the electrodes and unipolar impedances that connect from the electrode and form a circuit through tissue to a neutral connection, usually referred to as the patient return electrode, and finally returning to the instrument. The system 10 may be used to resolve 2N total impedance elements: N bipolar and N unipolar impedance elements, which result from the application of an N electrode catheter in contact with blood, pre-ablation cardiac tissue, post-ablation cardiac tissue, and/or ice formation on a cryoablation catheter.

Figure 8:
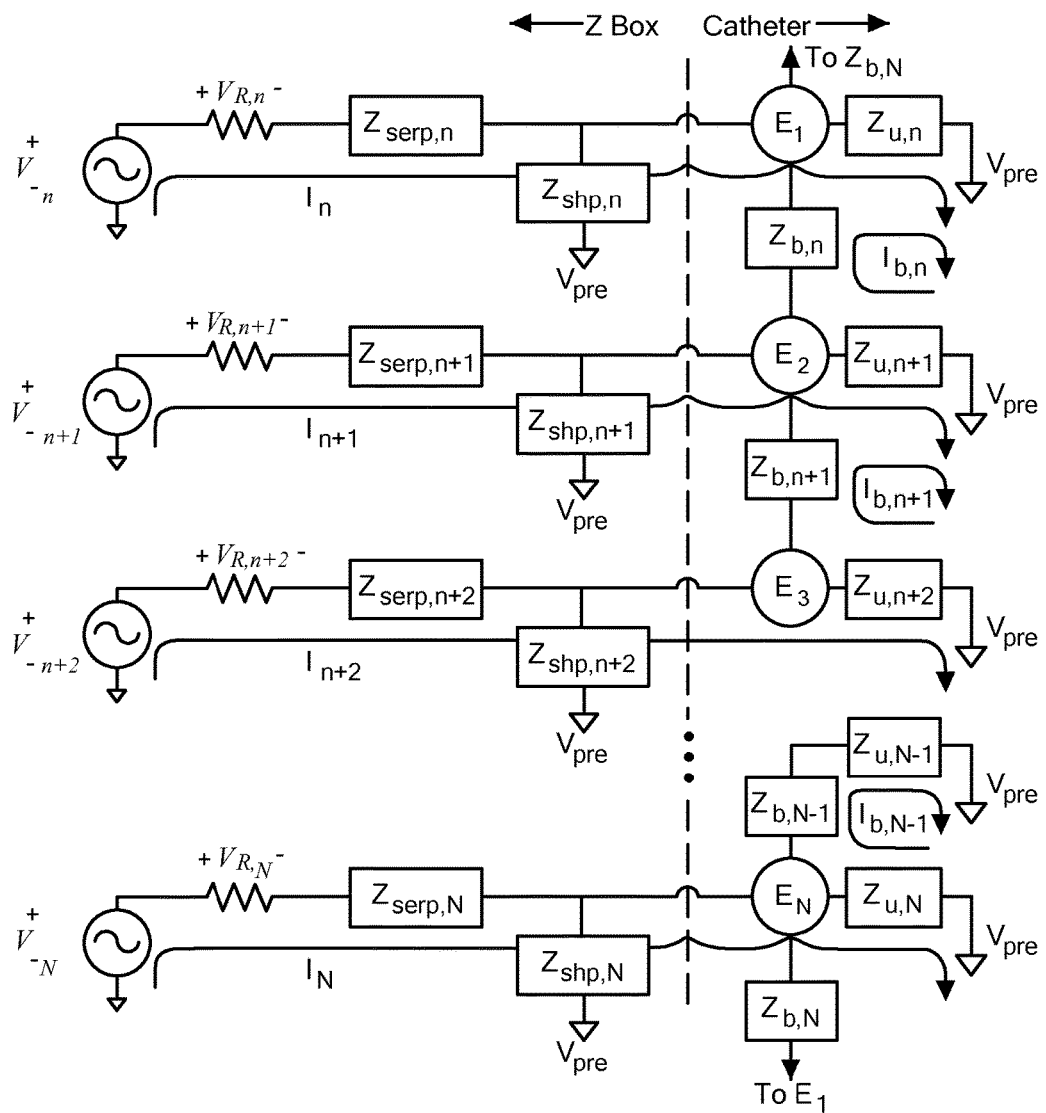
FIG. 8 shows a schematic view of a multi-electrode device impedance model.
Figure 9:
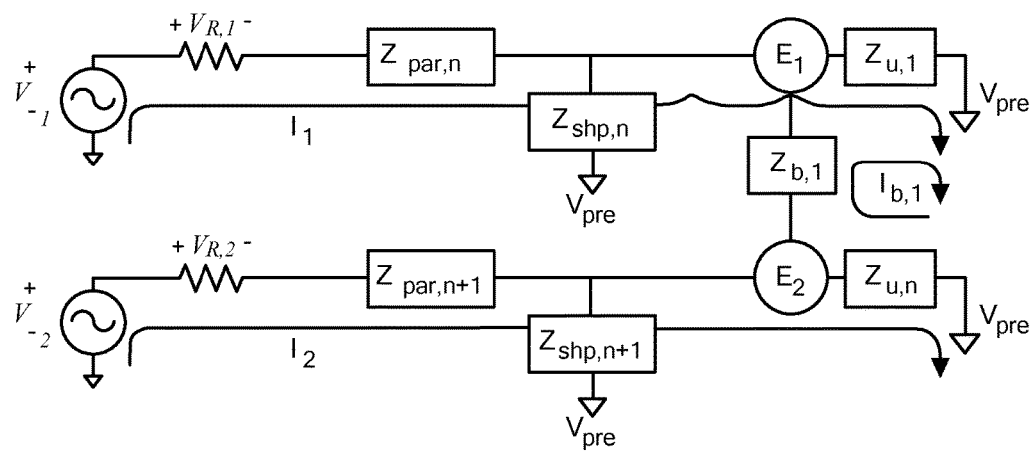
FIG. 9 shows a schematic view of a two-electrode device impedance model.

Referring to FIGS. 8 and 9, a set of linear equations ensue via application of Kirchoff's voltage law. Given N electrodes, there will be N unipolar and N bipolar impedance elements. The system of linear equations to solve the unipolar and bipolar impedances must then be:

$$Z = 2*2N - 1 \quad (9)$$

The solution to this system first may be solved analytically, leaving a set of formulae in a microcontroller that only require the voltage and current data from a set of analog-to-digital converters (ACDs). There are 2N ACDs: one to measure the source voltage $V_n$, and a second to infer the current formed by a voltage $V_{R,n}$, residing across a known resistance $R_n$.

As shown in FIG. 8, a catheter 12 may include N electrodes (depicted as $E_1$, $E_2$, $E_3$ ... $E_N$). Bipolar impedance $Z_{b,n}$ may exist between electrodes $E_1$ and $E_2$, bipolar impedance $Z_{b,n+1}$ may exist between electrodes $E_2$ and $E_3$, bipolar impedance $Z_{b,N-1}$ may exist between electrode $E_N$ and the next lowest numbered electrode (depending on how many electrodes 24 are included on the catheter 12). Finally, bipolar impedance $Z_{b,N}$ may exist between electrodes $E_N$ and $E_1$. Further, unipolar impedance $Z_{u,n}$ may exist between electrode $E_1$ and a patient return electrode (electrode not shown; pathway shown in FIG. 8 as $V_{pre}$), unipolar impedance $Z_{u,n+1}$ may exist between electrode $E_2$ and the patient return electrode ($V_{pre}$), unipolar impedance $Z_{u,n+2}$ may exist between electrode $E_3$ and the patient return electrode ($V_{pre}$), and unipolar impedance $Z_{u,N}$ may exist between electrode $E_N$ and the patient return electrode ($V_{pre}$). The circuit may also include parasitic impedance elements, depicted in FIG. 8 as $Z_{serp,n}$, $Z_{shp,n}$, $Z_{serp,n+1}$, $Z_{shp,n+1}$, $Z_{serp,n+2}$, $Z_{shp,n+2}$, $Z_{serp,N}$, and $Z_{shp,N}$.

Given this system of N electrodes, the number of unipolar and bipolar impedance elements is equal to two times the number of electrodes. That is:

$$Z = 2*2N - 1 \quad (9)$$

The number of unknowns and equations required to solve to calculate all the unipolar and bipolar impedances is:

$$\text{Equations} = 2*Z - 1 \quad (10)$$

In the circuit shown in FIG. 8, the known values may be $R_n$ ... $R_N$ (resistance values), $Z_{par,n}$ ... $Z_{par,N}$ (the parasitic impedances), and $V_n$ ... $V_N$ (voltage values at the nodes), and $V_{Rn}$ ... $V_{RN}$ (voltage values across the resistors). The unknown values may be $I_{b,n}$ ... $I_{b,N}$ (current values), $Z_{u,n}$ ... $Z_{u,N}$ (unipolar impedance values), and $Z_{b,n}$ ... $Z_{b,N}$ (bipolar impedance values).

In the simplified example shown in FIG. 9, the catheter 12 includes two electrodes, $E_1$ and $E_2$ and a patient return electrode (not shown). Similar to what is shown in FIG. 8, a bipolar impedance $Z_{b,1}$ may exist between electrodes $E_1$ and $E_2$, unipolar impedance $Z_{u,1}$ may exist between electrode $E_1$ and the patient return electrode, and unipolar impedance $Z_{u,2}$ may exist between electrode $E_2$ and the patient return electrode. Parasitic impedance values $Z_{par,n}$, $Z_{shp,n}$, $Z_{par,n+1}$, $Z_{shp,n+1}$ may also exist in the circuit (the abbreviation "shp" represents a shunt path). In this example, there are two electrodes 24, and three unknowns ($Z_{u,1}$, $Z_{u,2}$, and $Z_{b,1}$). So, N=2 electrodes and unknowns=3. The number of impedance elements is calculated as:

$$Z = 2*N - 1 = 3 \quad (11)$$

The number of equations to solve is calculated as:

$$\text{Equations} = 2*(Z) - 1 = 5 \quad (12)$$

A first measurement may be conducted that provides equations that are insufficient to the number of unknowns. To supply the remaining equations for a solution, a second condition may be applied that annihilates the current in a system pathway, rendering another set of equations that exceed the quantity of new unknowns. In combining the equations and unknowns from the first and second condition, equations and unknowns are balanced, and all of the desired unipolar and bipolar impedance elements can be found one. For example, three of the five equations to be solved may be solved with a first condition applied:

$$kvl_{I1}: V_1 = I_1(R_1 + Z_{par1} + Z_{u,1}) + I_{b,1}Z_{u,1} \quad (13)$$

$$kvl_{I2}: V_2 = I_2(R_2 + Z_{par2} + Z_{u,2}) + I_{b,1}Z_{u,2} \quad (14)$$

$$kvl_{Ib,1} = 0 = I_{b,1}(Z_{u,1} + Z_{u,2} + Z_{b,1}) + I_1 Z_{u,1} - I_2 Z_{u,2} \quad (15)$$

For the final two equations, a second condition may be applied, wherein $I_1 \neq 0$ and $I_2 = 0$:

$$kvl_{I1'}: V_{1'} = I_{1'}(R_1 + Z_{par1} + Z_{u,1}) + I_{b,1'}Z_{u,1} \quad (16)$$

$$kvl_{Ib,1'}: 0 = I_{b,1'}(Z_{u,1} + Z_{u,2} + Z_{b,1}) + I_{1'} Z_{u,1} \quad (17)$$

The abbreviation "kvl" represents Kirchoff's Voltage Law, which law may be used to relate the known quantities in the measurement circuit to the unknown quantities to be found.

Figure 11A:
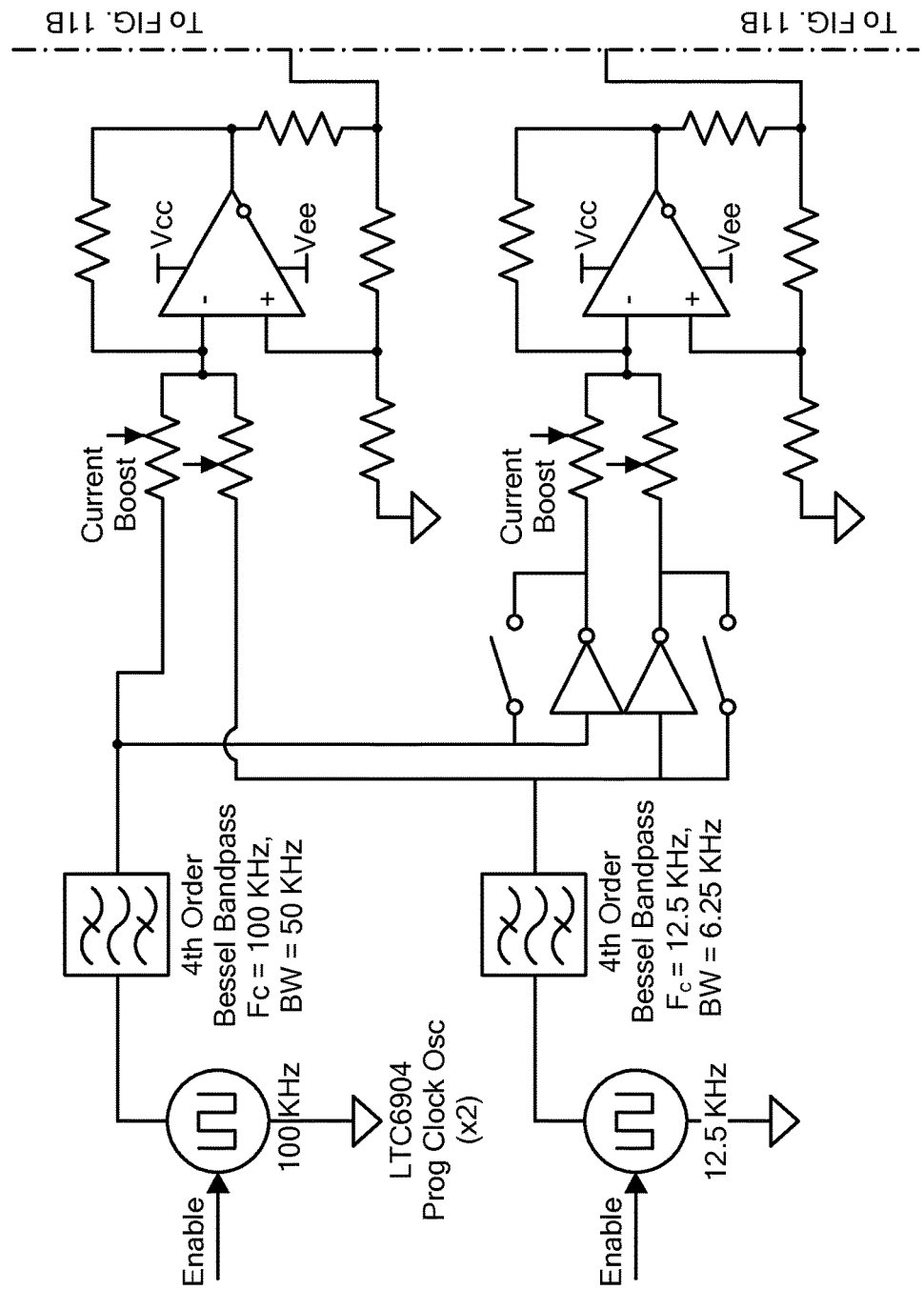
FIGS. 11A and 11B show a schematic view of a circuit implementation of a multi-frequency generator, Gaussian filtering, summing M frequencies, constant current waveform amplifiers, and a catheter electrode multiplexing system.
Figure 11B:
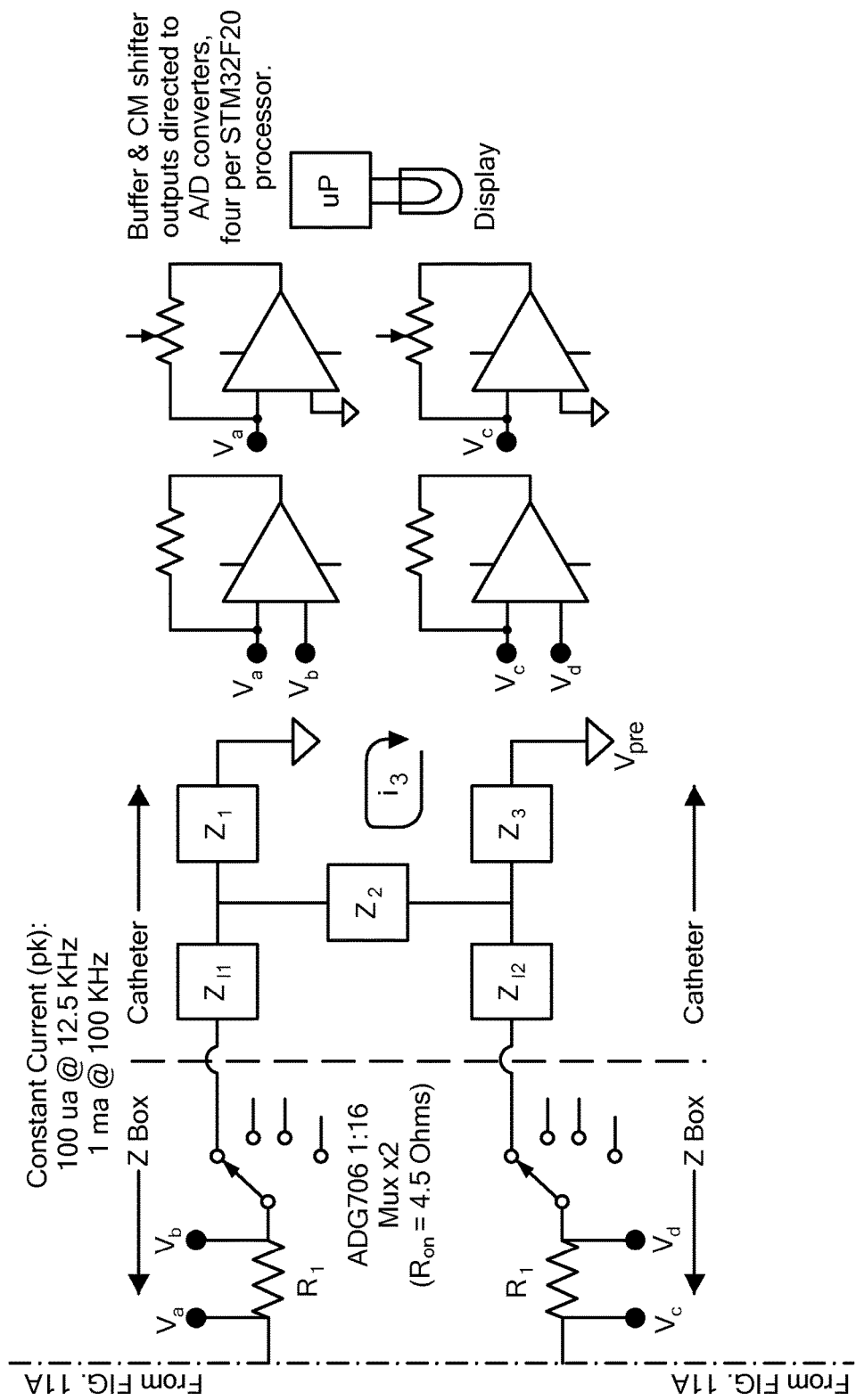

While executing the algorithm needed to solve for the unknown bipolar and unipolar impedances and currents shown in FIG. 9, a microcontroller may divert the constant current signals via the 2N switch array shown in FIGS. 11A and 11B as a 1:16 multiplexor to the appropriate catheter electrode. The switch array may be kept at a manageable size by requiring only 2 poles for N electrodes to solve for the respective 2N unipolar and bipolar impedances.

Figure 10:
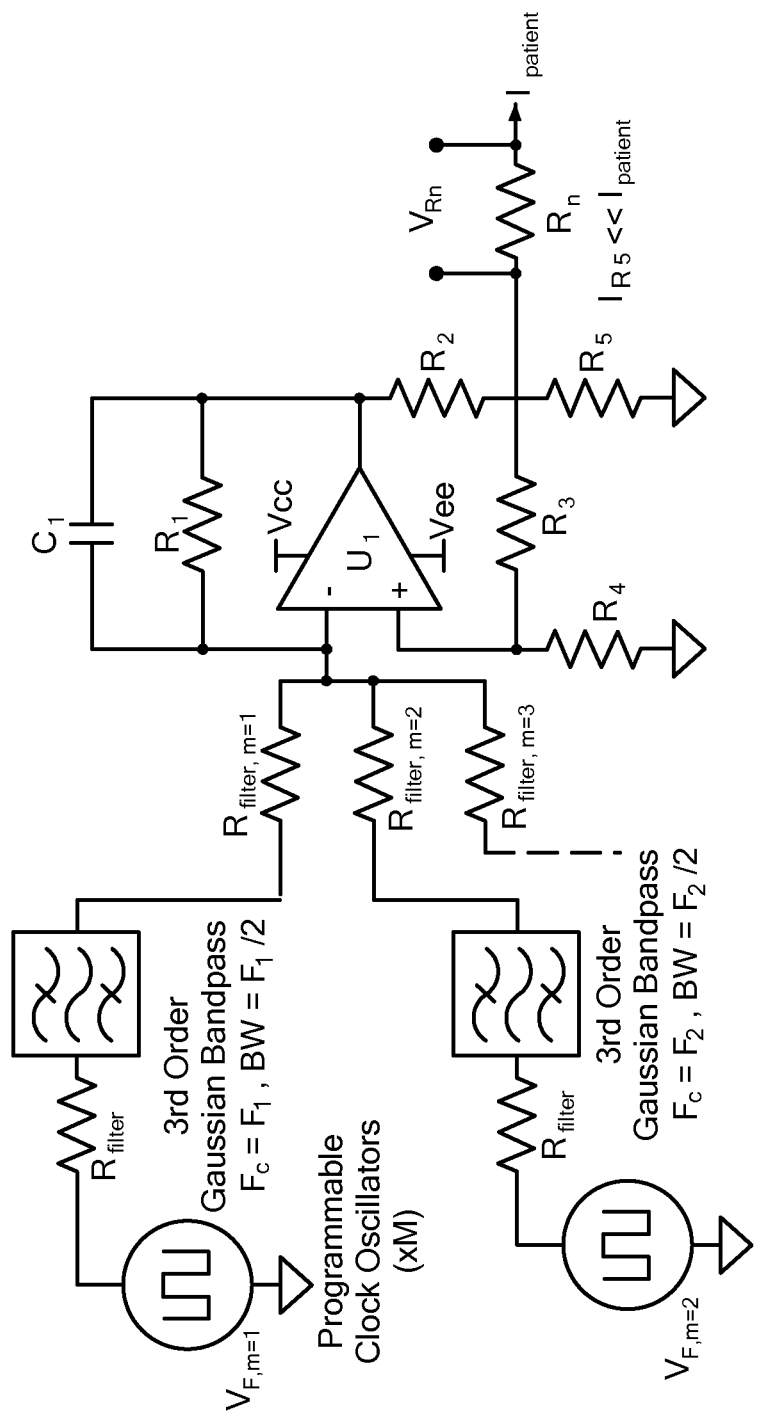
FIG. 10 shows a schematic view of a circuit implementation of a multi-frequency generator, Gaussian filtering, and summing M frequencies into one multi-spectral, constant current waveform without unipolar energy.

The system 10 may also maximize catheter delivered current consistent with applicable patient safety standards, minimize the risk of inadvertent cardiac or nerve stimulation by elimination of unipolar charge delivery, and deliver a multi-spectral measurement current that allows for the simultaneous measurement and resolution of unipolar and bipolar impedances. Referring now to FIGS. 10 and 11, schematic views of a corresponding circuit implementation are shown. The simultaneous excitation of multi-frequency waveform for each electrode may be accomplished using quantity M programmable and low-cost "chip" clock oscillators. The clock oscillators generate pulse waveforms that are applied to their respective Gaussian band-pass filters, which in turn may remove all artifacts except the fundamental sine waveform. By the nature of their dampened sinusoidal waveform outputs, Gaussian filtered signals may contain negligible amounts of unipolar energy. For example, a short (or "runt") pulse that would normally transfer unipolar energy if unfiltered may be removed to create a waveform with no evidence of unipolar energy following operation by a third-order Gaussian band-pass filter. Typically, unipolar charge delivered to a heart chamber must be less than 50 nC (50e-9 Coulombs) to insure no risk of stimulation and capture by the heart's atrium or ventricle. In FIGS. 11A and 11B, energy is transmitted in the high frequency (100 kHz) and low frequency (12.5 kHz).

After Gaussian filtering, a Howland constant current amplifier may be modified to enhance functionality. Once of these improvements may be in the form of a passive summation array that is used to create a composite waveform from individual sinusoids. The summation function may be accomplished by using a passive weighting function, whereby a discrete gain equal to: $R_1/R_{filter,m}$ may be applied to each individual frequency (monochrome) depending on the $R_{filter,m}$ weighting values. This operation ensures that each frequency constituent current is compliant with medical equipment safety standards, which stipulate that current delivered to patients via catheters 12 positioned in the heart must not exceed limits depending on frequency. To comply with recent International Electrotechnical Commission (IEC) standards, current delivered to heart chambers at a frequency of 10 kHz must not exceed 100 uA root mean square (rms), whereas current delivered to the heart at 100 can be ten times greater, but cannot exceed 1 mA rms. The relation for constant current may be calculated by:

$$\frac{R_2 + R_3}{R_4} = \frac{R_1}{(2R_{filter,m=1})\|(2R_{filter,m=2})\|(2R_{filter,m=3})\|\ldots} \quad (18)$$

Once the individual monochromes are combined into one multi-frequency composite waveform, the modified Howland current amplifier may provide a constant amplitude delivered patient current, regardless of tissue termination impedance, as long as a coordinated selection of resistors $R_{1-4}$ and $R_{filter,m}$ obey the constant current relationship shown in FIG. 10.

The circuit shown in FIG. 10 may improve the traditional Howland circuit in two primary ways. First, a capacitor $C_1$ may be added as a compensation capacitor that ensures that op-amp $U_1$'s closed-loop response (the bandwidth over which it provides a constant current function) remains stable and does not evidence peaking or self-sustaining oscillations. The value of $C_1$ may be selected to provide a "flat" closed loop response slightly higher than the highest frequency monochrome. As a non-limiting example, a value of 120 pF may be selected to assure a smooth response to a frequency of 100 kHz, the highest frequency monochrome in the composite waveform.

Second, a shunt path resistance $R_5$ may be added so that as the catheter 12 traverses between very high and low conductivity tissue, the op-amp $U_1$ always remains in its linear operating region. The current diverted to this shunt may be very small, typically less than 1% of the patient-delivered current, leaving the patient current constant within 99% of the maximum delivered amount, regardless of catheter electrode termination impedance. This function may be necessary to ensure that the op-amp does not saturate (or open circuit) and propagate a unipolar "glitch" to the patient.

The system 10 may further be used to measure and resolve unipolar and bipolar impedances simultaneously. Each of the N simultaneously measured electrodes 24 may be supported by a circuit to generate and measure the excitation current. For this reason it may be desirable to limit N to less than the total number of electrodes by multiplexing the generation and measurement circuitry to multiple electrodes (for example, as shown in FIGS. 11A and 11B). In this way it may be possible to trade off the measured speed achieved by simultaneously measuring electrodes for economy in circuit size and cost.

Figure 15:
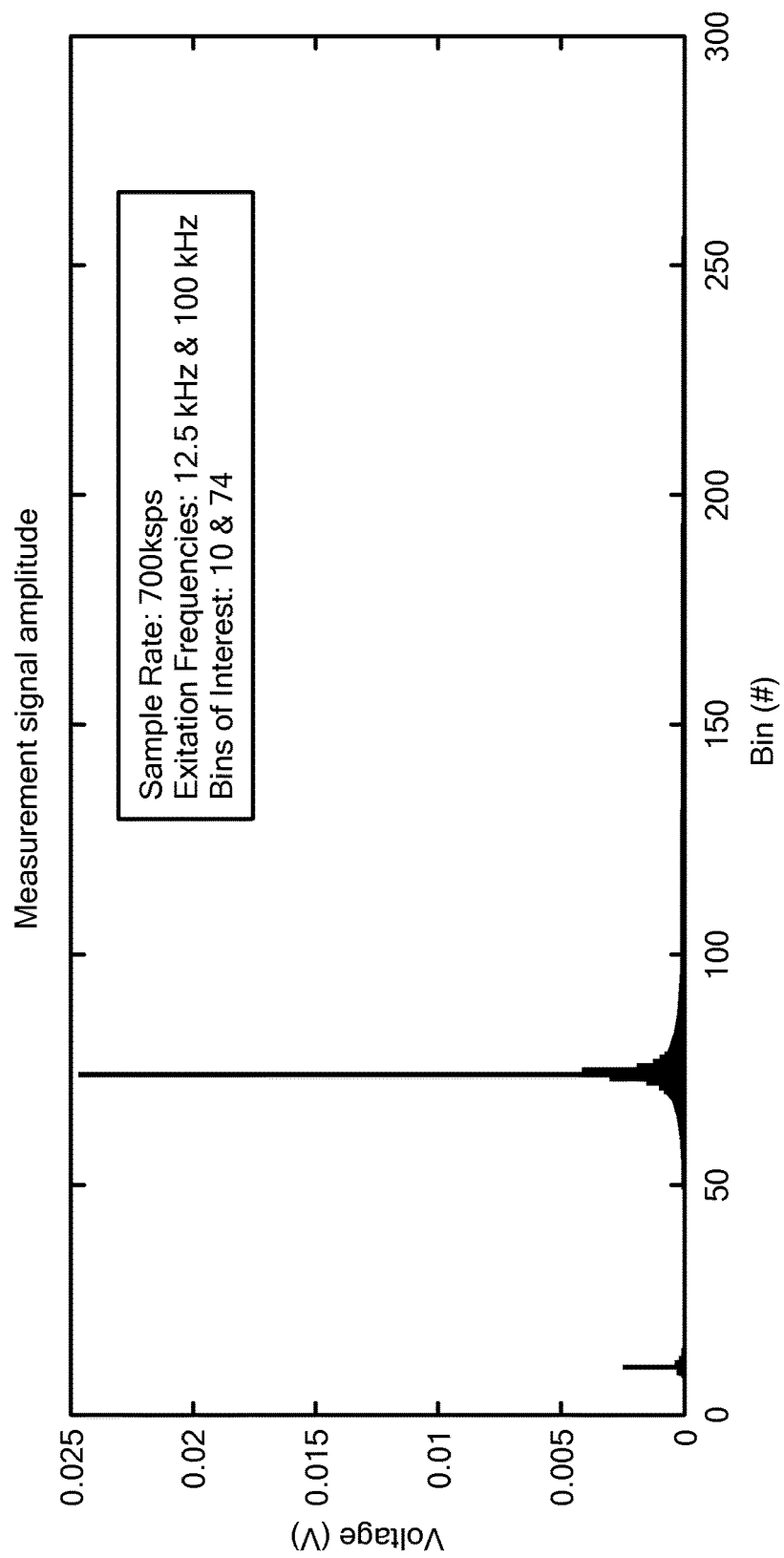
FIG. 15 shows a graphical view of a two-frequency patient-delivered current waveform in frequency domain.
Figure 16:
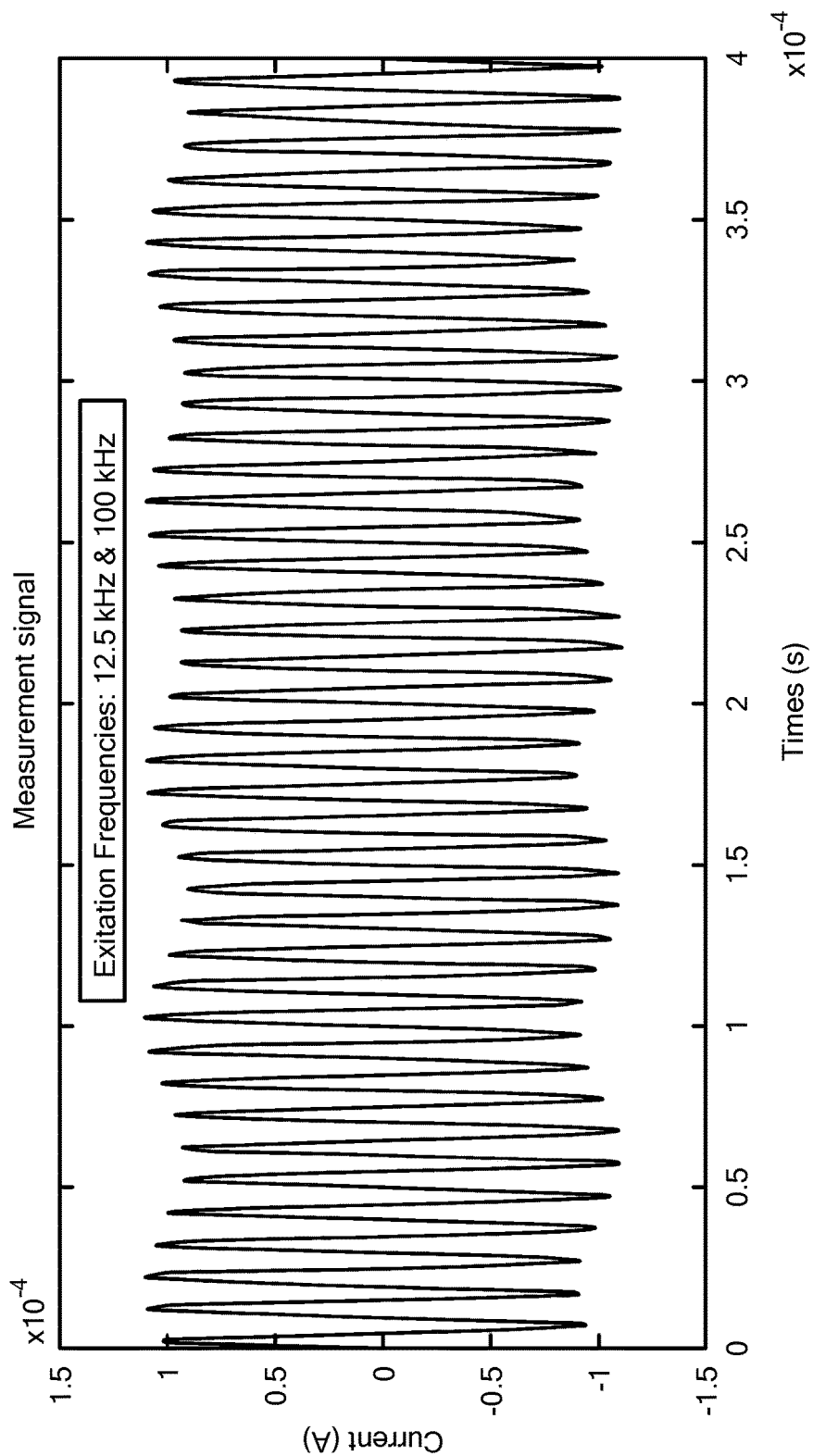
FIG. 16 shows a graphical view of a two-frequency patient-delivered current waveform in time domain.

Each of the N generation circuits may create an excitation current composed of the superposition of a constant-current phasor for every measurement frequency. For example, FIGS. 15 and 16 show non-limiting examples of an excitation signal composed of 10 uA 12.5 kHz and 100 uA 100 kHz signals in superposition. The excitation current may be passed through a sense resistor and out to the catheter electrodes 24, as shown in FIG. 8. Complex voltage at each frequency of interest may be measured at the output of each constant-current driver, and across each sense resistor. Next, one or more of the current drivers may be deactivated and the complex voltage measurement may be repeated. As shown in FIG. 9, the two sets of voltages may be sufficient to solve a system of equations of all unipolar and bipolar impedances.

The system 10 may further be used to measure, detect, and resolve catheter delivered multi-spectral, simultaneous measurement currents into their mono-frequency constituents. For example, it may be necessary to resolve the superimposed measurement currents into mono-frequency phasors before using them to determine impedance. As shown in FIG. 8, the voltage phasors $V_1 \ldots V_N$ and $V_{R1} \ldots V_{RN}$ may be determined by first taking a series of real voltage measurements across the corresponding elements. These samples are taken so that several periods of the slowest frequency are captured. A discrete Fourier transform may be applied to each series. A full transform may be computed, or a partial transform may be applied by only computing the results for the bins containing each excitation frequency. If a full transform is applied, the results for the excitation frequency bins may be kept and the rest discarded. Once the transform is complete, the complex results for the bins containing each frequency of interest may be taken to be the voltages $V_1 \ldots V_N$ and $V_{R1} \ldots V_{RN}$ at each frequency and used to solve the impedance calculations. For example, FIG. 15 shows the spectral amplitude of the measurement signal displayed in FIG. 16.

The system 10 may further be used to disambiguate unipolar and bipolar impedances from parasitic pathway impedances resulting from non-ideal catheter delivery wire impedance, inter-catheter wire field coupling mechanisms, and ablation delivery system signal splitter and filter conductive pathways and field coupling mechanisms. Parasitic pathways are inevitable in a distributed system containing an ablation generator 52, interfacing equipment to ECG monitors, catheter wires that exhibit impedance in the form of resistance and inductance ($Z=r+jX_i$), and capacitive coupling or shunting from one electrode's set of wires to another set of wires connected to other electrodes. Without extraction, these pathways will corrupt measured signals and render inaccurate catheter impedances.

Figure 12A:
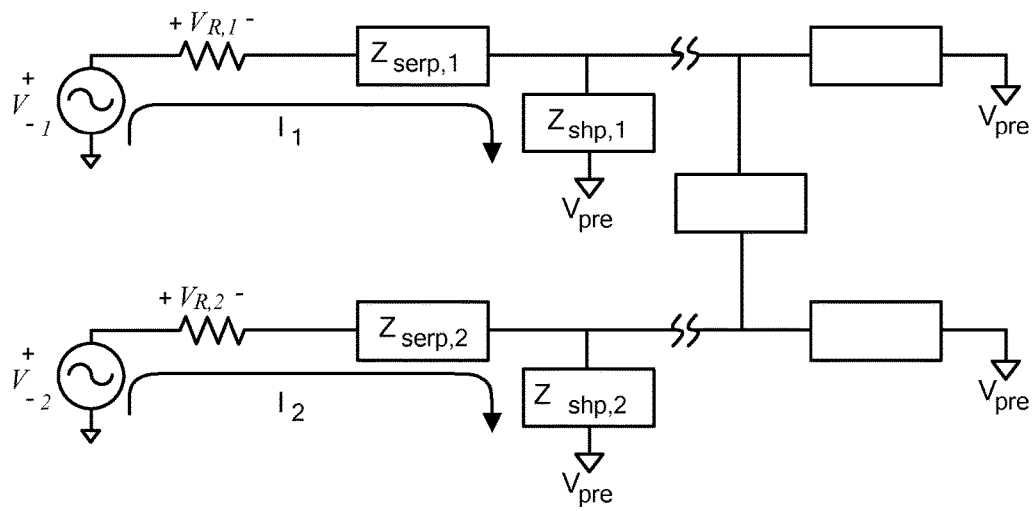
FIG. 12A shows a schematic view of a first exemplary calibration with Condition A, wherein parasitic series and shunt impedance elements are determined.
Figure 12B:
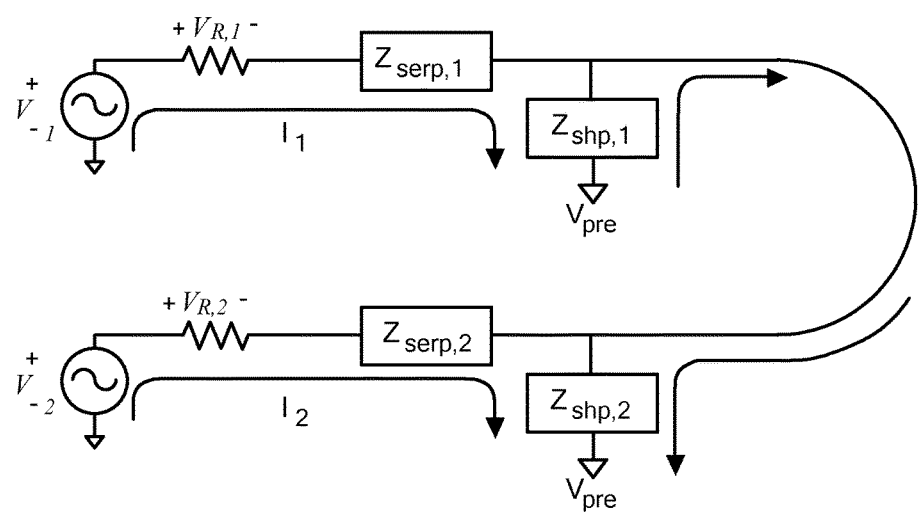
FIG. 12B shows a schematic view of a first exemplary calibration with Condition B, wherein parasitic series and shunt impedance elements are determined.
Figure 13:
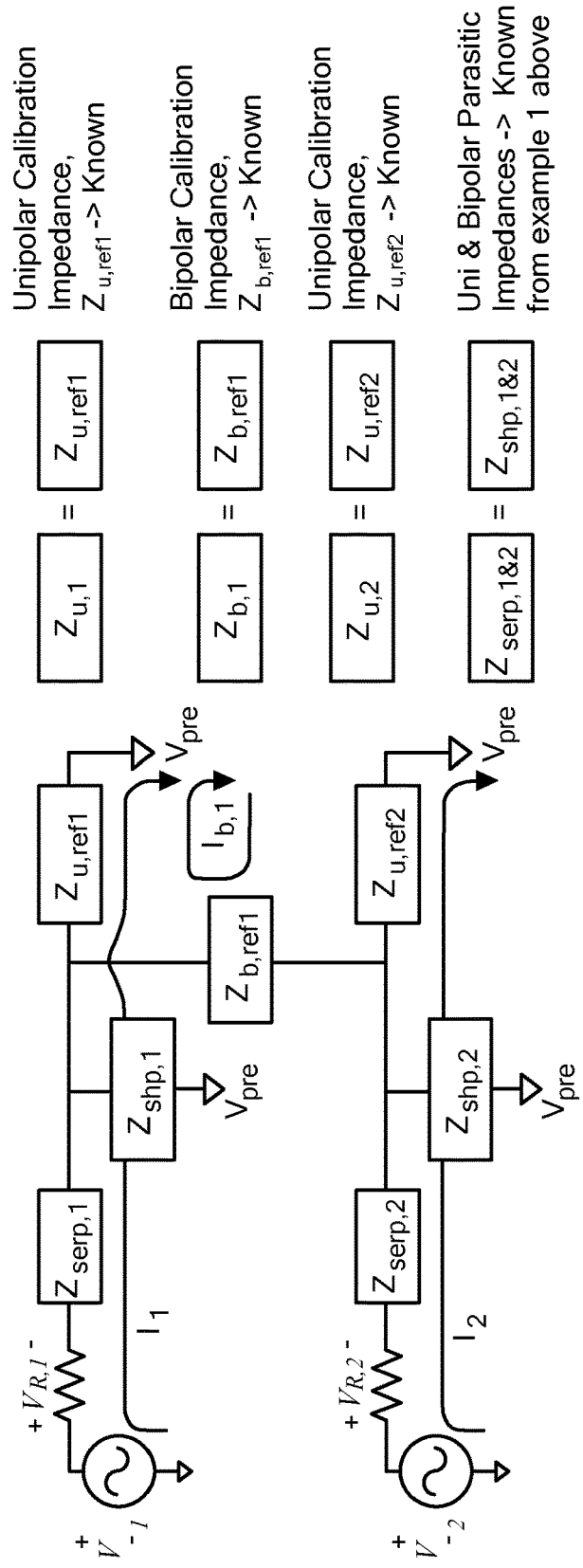
FIG. 13 shows a schematic view of a second exemplary calibration, wherein offsets are determined using traceable sources.

These parasitic impedances (or admittances) may be solved for and de-embedded from the desired catheter electrode impedance by defining a reference plane where the load is removed and left open (as shown in FIG. 12A). For example, this plane may be defined at the electrode plane of a catheter, such that all of the parasitic impedance effects could be accounted for and removed from unipolar and bipolar tissue impedance elements. For the two electrode case (for example, shown in FIG. 9), N=2, once the open circuit plane is defined, there may be two KVL loop equations with four parasitic elements: $Z_{serp1,2}$ and $Z_{shp1,2}$ as unknowns. The signal currents are applied, and the measurements may be taken at the voltage source nodes $V_1$ and $V_2$, as well as at the current inference nodes $V_{R1}$ and $V_{R2}$. Next, a short circuit may be placed from E and $E_2$ (for example, as shown in FIG. 12B). The short circuit may produce a second condition that creates 3 additional KVL loop equations, and only one more unknown, $i_{b,1}$. There are now five equations that balance the five unknowns. The parasitic impedance elements may then be solved, and their effect removed from catheter electrode impedance measurements.

Figure 14:
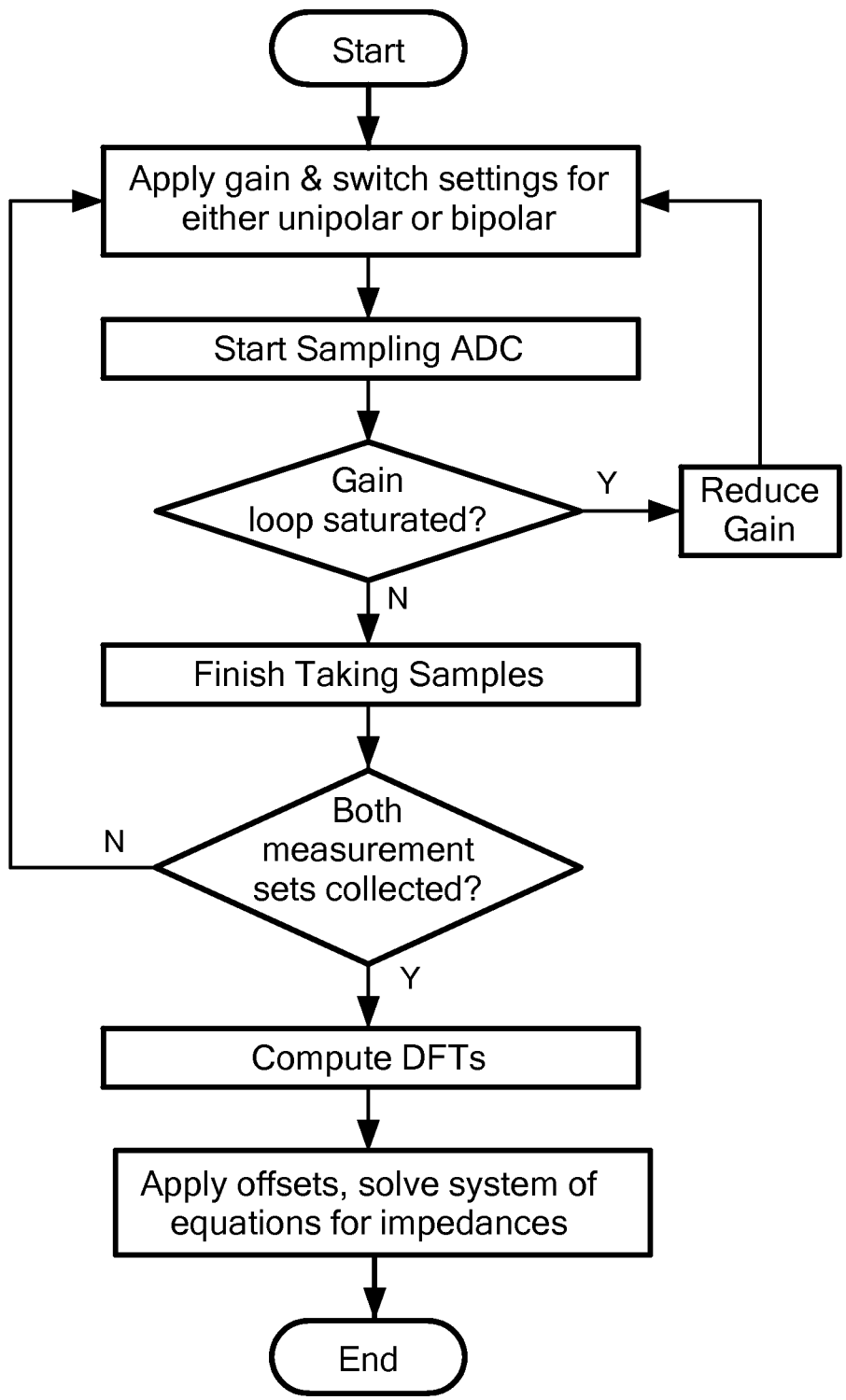
FIG. 14 shows a flow chart for gain adjustment.

The system 10 may further be used to adapt wide-ranging voltage and current measurements resulting from similarly wide-ranging values of blood, pre-ablation cardiac tissue, post-ablation cardiac tissue, and/or ice formation on a cryoablation catheter. In order to maintain a high signal-to-noise ratio (SNR) while allowing for a wide range of impedance magnitudes, a variable amount of gain may be needed between each voltage node ($V_1 \ldots V_N$ and $V_{R1} \ldots V_{RN}$ as shown in FIG. 8) and the ADC that measures the real voltage at that node. If too little gain is applied relative to the load impedance, and SNR, and thus the measurement reliability, may suffer. Conversely, if there is too much gain, the nonlinearities may be introduced as the signal is distorted or clips at the extremes of the ADC's measurement capabilities. To prevent this, each measurement may begin with a high amount of gain applied. If the ADC measures a value that is outside of the linear region in the center of its measurement capabilities, then all samples may be discarded, gain may be reduced, and measuring may be restarted. This sequence may be repeated until gain is sufficiently low that no samples are outside the linear region, at which point the sampled values may be saved and the impedance calculation may proceed. The gain adjustment process is shown in FIG. 14.

A set of high precision resistive and reactive standards may be assembled upon the impedance meter apparatus printed circuit board assembly, and then used as a special case measurement so that the impedances derived can be referred to in terms of absolute physical units of resistive and reactive ohms.

Calibration may be required because individual amplifiers and filters used in the impedance meter may produce non-ideal signal pathway bandwidths and phase responses, and because sampling may produce artifacts. So that the impedance meter can render accurate results, the meter may be calibrated to offset and nullify these non-idealities.

Assuming that parasitic impedances are accounted for, a highly precise set of resistive and reactive standards may be placed in positions emulating the catheter electrode unipolar and bipolar positions. These standards may then be referred to automatically via the switch array, and their values used as a reference by performing an impedance reading. While rendering a result, an internal microprocessor may compare the measured reading to a priori values of the precision internal resistive and reactive standards and correct the otherwise skewed measurement reading. The offset may then be recorded and applied to subsequent catheter unipolar and bipolar measurements.

Since it may be impractical for a physician to remove a catheter from an ablation generator, reconnect the catheter to a stand-alone impedance meter, and then reconnect to the ablation generator, some means should be provided to allow the impedance meter to remain connected to the generator 52 and the catheter 12. Yet, some means must also be provided that isolates and protects the impedance meter from the high level of radiofrequency energy (in cases wherein a radiofrequency generator is used) or high voltage (in cases wherein a pulsed field ablation generator is used) present on catheter wires that are simultaneously connected to the generator 52, ECG monitor 56, and the impedance meter 55.

Figure 17:
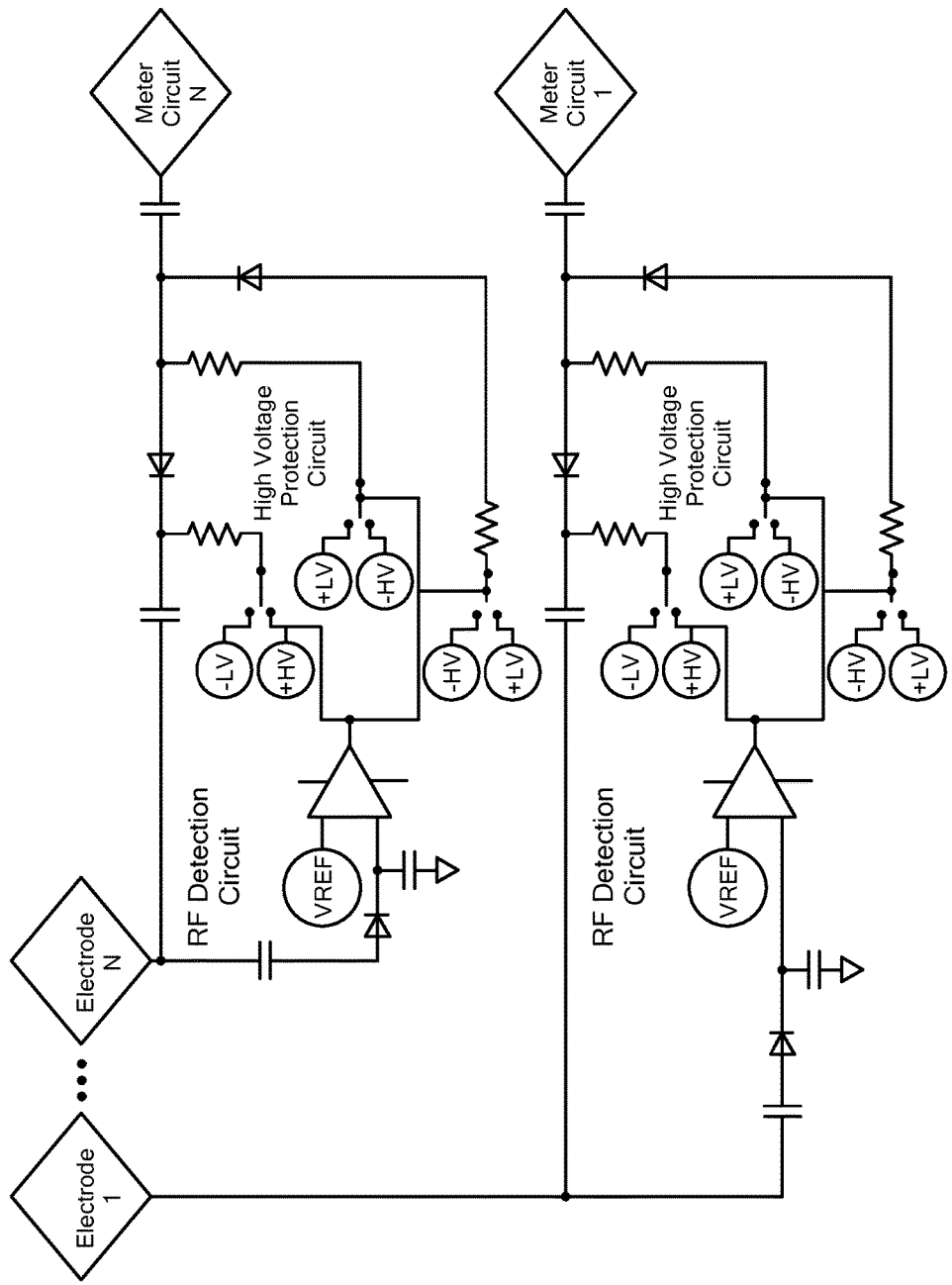
FIG. 17 shows a schematic view of an impedance meter isolation system.

A system 10 is shown in FIG. 17 that may isolate the impedance meter 55. During ablation, an inline PIN diode may be reverse biased to act as an open switch, preventing radiofrequency or high voltage energy from entering the impedance meter. During an impedance meter reading, the series PIN diode may be forward biased and create a highly conductive path to the catheter electrode wire, whereas the shunt PIN diode may be reversed biased and act as an open circuit.

A detector circuit may sense the application of ablation energy and instantaneously control the application of voltages necessary to correctly bias the two PIN electrodes. The automatic circuit may negate the need for communication of an on/off signal from the generator, allowing the impedance meter to be connected to a variety of ablation generators without concern of manufacture or revision of generator hardware or software.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for assessing electrode-tissue contact status, the system comprising:
   a medical device including a treatment assembly having a plurality of electrodes; and
   a control unit in communication with the medical device, the control unit programmed to:
      determine a first difference value, the first difference value being between a maximum impedance magnitude at a low frequency for one of a plurality of electrodes and an absolute minimum impedance magnitude at the low frequency across all of the plurality of electrodes, the low frequency being between 5 kHz and 15 kHz;
      determine a second difference value, the second difference value being between a maximum impedance magnitude at a high frequency for the one of the plurality of electrodes and an absolute minimum impedance magnitude at the high frequency across all of the plurality of electrodes, the high frequency being between 80 kHz and 140 kHz;
      determine a third difference value, the third difference value being between a maximum impedance phase at the high frequency for the one of the plurality of electrodes and an absolute minimum impedance phase at the high frequency kHz across all of the plurality of electrodes;
      compare the first, second, and third difference values to each other for each of the plurality of electrodes, the comparison including applying a linear model to each of the first, second, and third difference values;
      assign to each of the plurality of electrodes a discrete prediction value based on the comparisons, the assigned discrete prediction value indicating electrode-tissue contact status, the control unit assigning a discrete prediction value of 0 to any electrode of the plurality of electrodes that is not in contact with tissue and assigning a discrete prediction value of 1 to any electrode of the plurality of electrodes that is in contact with tissue; and deliver ablation energy to any electrode of the plurality of electrodes to which a discrete prediction value of 1 is assigned.

2. The system of claim 1, wherein the low frequency is 12.5 kHz.

3. The system of claim 1, wherein the high frequency is 100 kHz.

4. The system of claim 1, wherein the control unit is further programmed to assign a discrete prediction value of 2 to an electrode when the electrode is in excessive contact with tissue.

5. A system for assessing electrode-tissue contact status, the system comprising:
a medical device including a treatment assembly having a plurality of electrodes; and
a control unit in communication with the medical device, the control unit programmed to:
record an impedance magnitude value at a first frequency by each of a plurality of electrodes and determine a maximum impedance magnitude value of the plurality of impedance magnitude values at the first frequency;
record an impedance magnitude value at a second frequency by each of the plurality of electrodes and determine a maximum impedance magnitude value of the plurality of impedance magnitude values at the second frequency;
record an impedance phase value at the second frequency by each of the plurality of electrodes and determine a maximum impedance phase value of the plurality of impedance phase values;
record a minimum impedance magnitude value at the first frequency across all of the plurality of electrodes;
record a minimum impedance magnitude value at the second frequency across all of the plurality of electrodes;
record a minimum impedance phase value at the second frequency across all of the plurality of electrodes;
for each of the plurality of electrodes, calculate a first difference value between the maximum impedance magnitude value and the minimum impedance magnitude value recorded at the first frequency;
for each of the plurality of electrodes, calculate a second difference value between the maximum impedance magnitude value and the minimum impedance magnitude value recorded at the second frequency;
for each of the plurality of electrodes, calculate a third difference value between the maximum impedance phase value and the minimum impedance phase value recorded at the second frequency;
for each of the plurality of electrodes, apply a linear model to all of the first, second, and third difference values to determine a continuous prediction value for each of the plurality of electrodes;
assign a discrete prediction value to each of the plurality of electrodes based on a corresponding continuous prediction value, a discrete prediction value of 0, indicating no tissue contact, being assigned to a continuous prediction value that is less than a cutoff value and a discrete prediction value of 1, indicating tissue contact, being assigned to a continuous prediction value that is at least the cutoff value; and deliver ablation energy to any electrode of the plurality of electrodes to which the control unit assigns a discrete prediction value of 1; and
a display in communication with the control unit.

6. The system of claim 5, wherein a continuous prediction value for each of the plurality of electrodes is determined using the equation:

$$\text{continuous prediction value} = a*1 + b*\Delta Z_{100} + c*\Delta Z_{12.5} + d*\Delta \varnothing_{100},$$

where:
a, b, c, and d are coefficients;
$\Delta Z_{100}$ is a difference in impedance magnitude at the second frequency;
$\Delta Z_{12.5}$ is a difference in impedance magnitude at the first frequency; and
$\Delta \varnothing_{100}$ is a difference in impedance phase at the second frequency.

7. The system of claim 5, wherein the display is configured to display at least one of the continuous prediction value for each of the plurality of electrodes and the discrete prediction value for each of the plurality of electrodes.

8. The system of claim 7, wherein the at least one of the continuous prediction value and the discrete prediction value is displayed in at least one of text, color, and graphical formats.

9. The system of claim 8, wherein a graphical representation of the plurality of electrodes is displayed, each of the plurality of electrodes being displayed as a color that corresponds to at least one of the continuous prediction value and the discrete prediction value, the colors changing in real time with the at least one continuous prediction value and discrete prediction value.

10. The system of claim 5, wherein the second frequency is higher than the first frequency.

11. The system of claim 10, wherein the first frequency is between approximately 5 kHz and approximately 15 kHz.

12. The system of claim 11, wherein the first frequency is 12.5 kHz.

13. The system of claim 10, wherein the second frequency is between approximately 80 kHz and approximately 140 kHz.

14. The system of claim 13, wherein the second frequency is 100 kHz.

15. The system of claim 7, wherein the continuous prediction value is a number between 0 and 1.

16. The system of claim 5, wherein the cutoff value is 0.4.

17. The system of claim 5, wherein the cutoff value is 0.5.

18. The system of claim 7, wherein the continuous prediction value is a number equal to or greater than 0.

19. The system of claim 5, wherein the cutoff value is a first cutoff value, a discrete prediction value of 1 being assigned to a continuous prediction value that is at least the first cutoff value and less than a second cutoff value, and a discrete prediction value of 2 being assigned to a continuous prediction value that is at least the second cutoff value.

20. The system of claim 19, wherein the first cutoff value is 0.4 and the second cutoff value is 1.5.

21. A system for displaying electrode-tissue contact status, the system comprising:
a medical device including a treatment assembly having a plurality of electrodes; and
a control unit in communication with the medical device, the control unit programmed to:
record a first maximum impedance magnitude value from each of a plurality of electrodes at 12.5 kHz;

record a second maximum impedance magnitude value from each of the plurality of electrodes at 100 kHz;
record a maximum impedance phase value from each of the plurality of electrodes at 100 kHz;
record a first minimum impedance magnitude value across all electrodes of the plurality of electrodes at 12.5 kHz;
record a second minimum impedance magnitude value across all electrodes of the plurality of electrodes at 100 kHz;
record a minimum impedance phase value across all electrodes of the plurality of electrodes at 100 kHz;
determine a first difference value between the first maximum impedance magnitude value for each of the plurality of electrodes and the first minimum impedance magnitude value;
determine a second difference value between the second maximum impedance magnitude value for each of the plurality of electrodes and the second minimum impedance magnitude value;
determine a third difference value between the maximum impedance phase value for each of the plurality of electrodes and the minimum impedance phase value;
apply a linear model to each of the first, second, and third difference values to determine a continuous prediction value between 0 and 1 for each of the plurality of electrodes; and
assign a discrete prediction value of 0 to each of the plurality of electrodes for which the continuous prediction value is less than a cutoff value and assign a discrete prediction value of 1 to each of the plurality of electrodes for which the continuous prediction value is equal to or greater than the cutoff value; and
deliver ablation energy to any of the plurality of electrodes to which a discrete prediction value of 1 is assigned; and
a display in communication with the control unit, the display configured to display at least one of the continuous prediction value for each of the plurality of electrodes and the discrete prediction value for each of the plurality of electrodes in at least one of text, color, and graphical formats.

* * * * *